United States Patent
Rangnekar

(10) Patent No.: US 10,512,641 B2
(45) Date of Patent: Dec. 24, 2019

(54) CHLOROQUINE INDUCTION PAR-4 AND TREATMENT OF CANCER

(71) Applicant: University of Kentucky Research Foundation, Lexington, KY (US)

(72) Inventor: Vivek M. Rangnekar, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/576,366

(22) PCT Filed: Jun. 1, 2016

(86) PCT No.: PCT/US2016/035239
§ 371 (c)(1),
(2) Date: Nov. 22, 2017

(87) PCT Pub. No.: WO2016/196614
PCT Pub. Date: Dec. 8, 2016

(65) Prior Publication Data
US 2018/0147197 A1   May 31, 2018

Related U.S. Application Data

(60) Provisional application No. 62/169,406, filed on Jun. 1, 2015.

(51) Int. Cl.
| | |
|---|---|
| *A61K 31/4706* | (2006.01) |
| *A61P 35/04* | (2006.01) |
| *A61P 35/00* | (2006.01) |
| *A61K 31/122* | (2006.01) |
| *A61K 31/192* | (2006.01) |

(52) U.S. Cl.
CPC ........ *A61K 31/4706* (2013.01); *A61K 31/122* (2013.01); *A61K 31/192* (2013.01); *A61P 35/00* (2018.01); *A61P 35/04* (2018.01)

(58) Field of Classification Search
CPC ................ A61K 31/122; A61K 31/192; A61K 31/4706; A61P 35/00; A61P 35/04
See application file for complete search history.

(56) References Cited

U.S. PATENT DOCUMENTS

| | | | | |
|---|---|---|---|---|
| 5,340,803 | A * | 8/1994 | Rubin ..................... | A61K 31/05 514/25 |
| 7,786,275 | B2 * | 8/2010 | Rangnekar ............. | C07H 21/04 435/320.1 |
| 8,653,083 | B2 * | 2/2014 | Beachy ................ | A61K 31/365 514/254.07 |
| 9,873,670 | B2 * | 1/2018 | Watt ...................... | C07D 215/38 |
| 2005/0118179 | A1 | 6/2005 | Rangnekar | |

FOREIGN PATENT DOCUMENTS

EP         2561868 A1 *  2/2013  ............ A61K 45/06
WO   WO 2015/077550 A1   5/2015

OTHER PUBLICATIONS

Nalca et al., "Oncogenic Ras Sensitizes Cells to Apoptosis by Par-4", 1999, J. Biol. Chem., vol. 274, No. 42, pp. 29976-29983. (Year: 1999).*
Chakraborty et al., "Par-4 Drives Trafficking and Activation of Fas and FasL to Induce Prostate Cancer Cell Apoptosis and Tumor Regression", 2001, Cancer Res., 61(19), pp. 7255-7263. (Year: 2001).*
Abdel-Aziz et al., "Chloroquine synergizes sunitinib cytotoxicity via modulating autophagic, apoptotic and angiogenic machineries", 2014, Chemico-Biological Interactions, vol. 217, pp. 28-40. (Year: 2014).*
Burikhanov et al., "Chloroquine-Inducible Par-4 Secretion Is Essential for Tumor Cell Apoptosis and Inhibition of Metastasis", 2017, Cell Reports, vol. 18, Issue 2, pp. 508-519. Reports (Year: 2017).*
Sells et al., "Expression and Function of the Leucine Zipper Protein Par-4 in Apoptosis", 1997, Molecular and Cellular Biology, 17(7), pp. 3823-3832. (Year: 1997).*
Solomon et al., "Chloroquine and its analogs: A new promise of an old drug for effective and safe cancer therapies", 2009, European Journal of Pharmacology, 625(1-3), pp. 220-233 (Year: 2009).*
Cheng-Xiong et al., "Augmentation of NVP-BEZ235's anticancer activity against human lung cancer cells by blockage of autophagy", 2011, Cancer Biology & Therapy, 12(6), pp. 549-555. (Year: 2011).*
Wang et al., "Neoadjuvant administration of hydroxychloroquine in a phase 1 clinical trial induced plasma Par-4 levels and apoptosis in diverse tumors", 2018, Genes & Cancer, 9(5-6), pp. 190-197. (Year: 2018).*
International Search Report (PCT/ISA/210) issued in PCT Application No. PCT/US2016/035239 dated Oct. 6, 2016 (3 pages).
Written Opinion (PCT/ISA/237) issued in PCT Application No. PCT/US2016/035239 dated Oct. 6, 2016 (5 pages).
El-Guendy et al., "Identification of a Unique Core Domain of Par-4 Sufficient for Selective Apoptosis Induction in Cancer Cells", Molecular and Cellular Biology, Aug. 2003, pp. 5516-5525, vol. 23, No. 16.
Burikhanov et al., "A Novel Extrinsic Pathway Apoptosis by Tumor Suppressor Par-4", Cell., Jul. 23, 2009, pp. 377-388, vol. 138, No. 2.
Shrestha-Bhattarai et al., "Cancer-Selective Apoptotic Effects of Extracellular and Intracellular Par-4", Oncogene, 2010, pp. 3873-3880, vol. 29.
Zhao eta l., "Systemic Par-4 Inhibits Non-Autochthonous Tumor Growth", Cancer Biology and Therapy, Jul. 15, 2011, pp. 15-157, vol. 12, No. 2.
Burikhanov et al., "Paracrine Apoptotic Effect of p53 Mediated by Tumor Suppressor Par-4", Cell Rep., Jan. 30, 2014, pp. 271-277, vol. 6, No. 2.

(Continued)

*Primary Examiner* — My-Chau T. Tran
(74) *Attorney, Agent, or Firm* — Crowell & Moring LLP

(57) ABSTRACT

Described herein are methods for treating cancer in a subject in need thereof by administering chloroquine, or a salt or prodrug thereof, optionally with another agent that promotes Par-4 production to induce prostate apoptosis response-4 (Par-4) production by host cells, particularly non-cancerous host cells, to promote apoptosis in cancer cells, including androgen insensitive prostate cancer cells.

13 Claims, 19 Drawing Sheets

Specification includes a Sequence Listing.

(56) References Cited

OTHER PUBLICATIONS

Burikhanov et al., "Arylquins Target Vimentin to Trigger Par-4 Secretion for Tumor Cell Apoptosis", Nat Chem Biol., Nov. 2014, pp. 924-926, vol. 10, No. 11.
Burikhanov et al., "Novel Mechanism of Apoptosis Resistance in Cancer Mediated by Extracellular PAR-4", Cancer Res., Jan. 15, 2013, pp. 1011-1019, vol. 73, No. 2.
Kimura et al., "Chloroquine in Cancer Therapy: A Double-Edged Sword of Autophagy", American Association for Cancer Research, 2012, pp. 3-7, vol. 73, No. 1.
Dupont et al., "Autophagy-Based Unconventional Secretory Pathway for Extracellular Delivery of IL-1β", The EMBO Journal, 2011, pp. 4701-4711, vol. 30.
Jiang et al., "Secretory Versus Degradative Autophagy: Unconventional Secretion of Inflammatory Mediators", Journal of Innate Immunity, Feb. 22, 2013, nine (9) pages total.
Khan et al., "Future of Radiation Therapy for Malignant Melanoma in an Era of Newer, More Effective Biological Agents", Onco Targets and Therapy, 2011, pp. 137-148, vol. 4.
Burikhanov et al., "Novel Mechanism of Apoptosis Resistance in Cancer Mediated by Extracellular PAR-4", Cancer Res, Nov. 30, 2012, pp. 1011-1019, vol. 73, No. 2.
Thayyullathil et al., "ROS-Dependent Prostate Apoptosis Response-4 (Par-4) Up-Regulation and Ceramide Generation are the Prime Signaling Events Associated with Curcumin-Induced Autophagic Cell Death in Human Malignant Glioma", FEBS Open Bio, 2014, pp. 763-776, vol. 4.
Azmi et al., "Chemoprevention of Pancreatic Cancer: Characterization of Par-4 and its Modulation by 3, 3' Diindolylmethane (DIM)", Pharm Res., Sep. 2008, pp. 2117-2124, vol. 25, No. 9.
Srinivasan et al., "Par-4-Dependent Apoptosis by the Dietary Compound Withaferin A in Prostate Cancer Cells", Cancer Res, Jan. 1, 2007, pp. 246-253, vol. 67, No. 1.
International Preliminary Report on Patentability (PCT/IB/326 & PCT/IB/373) issued in PCT Application No. PCT/US2016/035239 dated Dec. 14, 2017, (7 pages).

* cited by examiner

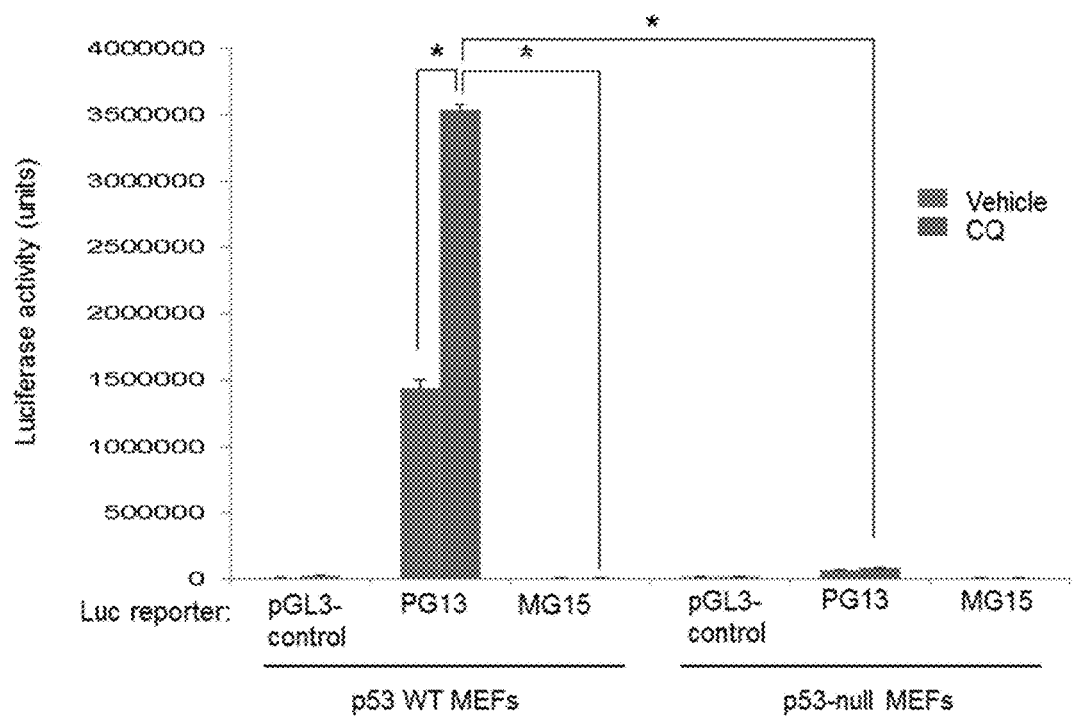
FIG 8A
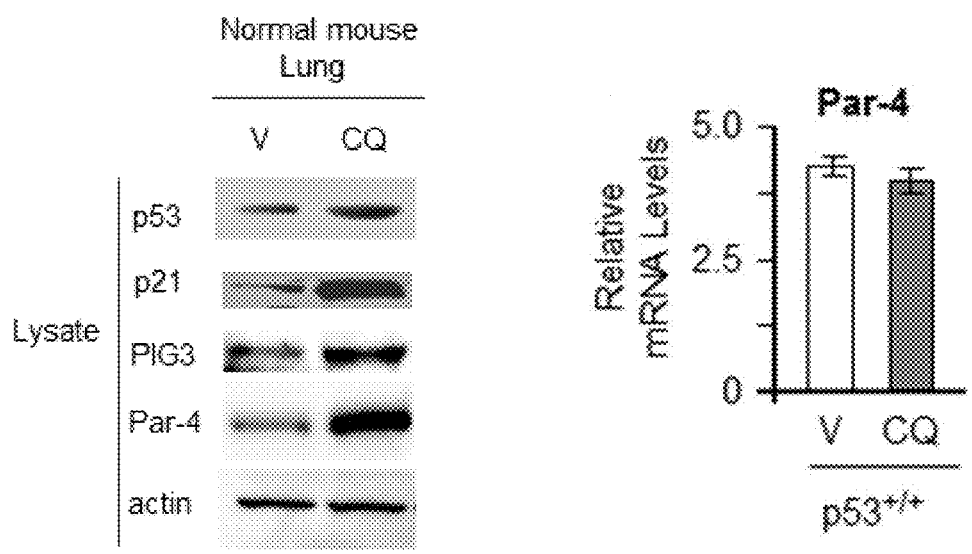
FIG 8B
FIG 8C

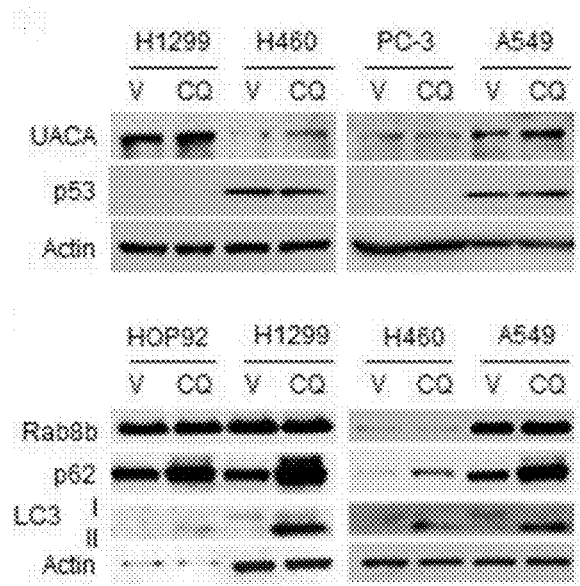
FIG 8D
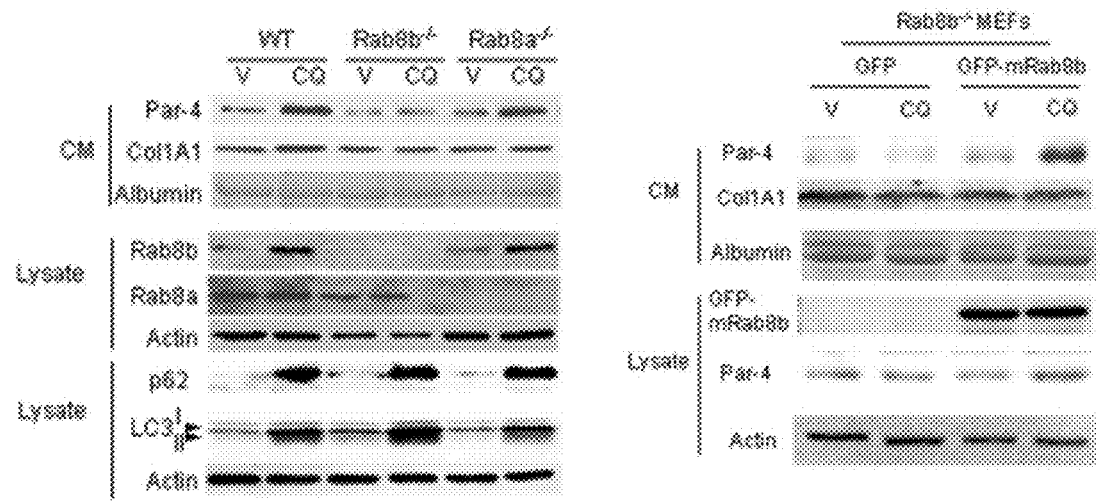
FIG 9A                    FIG 9B

SEQUENCE LISTING

<160> NUMBER OF SEQ ID NOS: 11

<210> SEQ ID NO 1
<211> LENGTH: 29
<212> TYPE: DNA
<213> ORGANISM: Artificial sequence
<220> FEATURE:
<223> OTHER INFORMATION: Synthesized sequence

<400> SEQUENCE: 1
rrrcwwgyyy rrrccccwwg ggggggyyy                                    29

<210> SEQ ID NO 2
<211> LENGTH: 21
<212> TYPE: DNA
<213> ORGANISM: Homo sapiens

<400> SEQUENCE: 2
ggggcacgcc cgaggctccc c                                            21

<210> SEQ ID NO 3
<211> LENGTH: 20
<212> TYPE: DNA
<213> ORGANISM: Mus musculus

<400> SEQUENCE: 3
ggagagccgc gggcgtgcct                                              20

<210> SEQ ID NO 4
<211> LENGTH: 20
<212> TYPE: DNA
<213> ORGANISM: Artificial sequence
<220> FEATURE:
<223> OTHER INFORMATION: Synthesized sequence

<400> SEQUENCE: 4
ctggcactcg actatgggat                                              20

<210> SEQ ID NO 5
<211> LENGTH: 20
<212> TYPE: DNA
<213> ORGANISM: Artificial sequence
<220> FEATURE:
<223> OTHER INFORMATION: Synthesized sequence

<400> SEQUENCE: 5
tttgctttga tatccctggc                                              20

<210> SEQ ID NO 6
<211> LENGTH: 20
<212> TYPE: DNA
<213> ORGANISM: Artificial sequence
<220> FEATURE:
<223> OTHER INFORMATION: Synthesized sequence

<400> SEQUENCE: 6
cacgcctctt cagatgttga                                              20

<210> SEQ ID NO 7
<211> LENGTH: 20
<212> TYPE: DNA
<213> ORGANISM: Artificial sequence
<220> FEATURE:
<223> OTHER INFORMATION: Synthesized sequence

<400> SEQUENCE: 7
cgactttgca cttgtctcca                                              20

<210> SEQ ID NO 8
<211> LENGTH: 20
<212> TYPE: DNA
<213> ORGANISM: Artificial sequence
<220> FEATURE:

```
<223> OTHER INFORMATION: Synthesized sequence

<400> SEQUENCE: 8
atcttctggg gcactggttg                                              20

<210> SEQ ID NO 9
<211> LENGTH: 20
<212> TYPE: DNA
<213> ORGANISM: Artificial sequence
<220> FEATURE:
<223> OTHER INFORMATION: Synthesized sequence

<400> SEQUENCE: 9
atcttctggg gcactggttg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthesized sequence

<400> SEQUENCE: 10
gtgaggcaaa agggaaggtg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthesized sequence

<400> SEQUENCE: 11
aggcatggca gattcagagt                                              20
```

CHLOROQUINE INDUCTION PAR-4 AND TREATMENT OF CANCER

This application claims priority to U.S. provisional application No. 62/169,406 filed Jun. 1, 2015, the disclosure of which is incorporated herein by reference in its entirety.

FIELD OF THE INVENTION

The present invention relates to methods for treating cancer in a subject by administering chloroquine to a subject in need thereof. The chloroquine is administered in amounts sufficient to induce production and/or secretion of the tumor suppressor prostate apoptosis response-4 ("Par-4") by normal cells, preferably in an amount sufficient to inhibit proliferation and/or metastasis of cancer cells, and/or reduce the recurrence of tumors. The chloroquine may be administered with or without a chemotherapeutic and optionally may be administered with curcumin and/or ibuprofen. The chloroquine may also optionally be administered with ionizing radiation.

BACKGROUND OF THE INVENTION

The development and progression of cancer is a multistep process involving accumulation of multiple genetic aberrations. Most notable among such aberrations is the loss of apoptotic responses that normally serve as built in checkpoints against the emergence of cell populations with dysfunctional traits or the acquisition of pro-survival mechanisms that override the apoptotic signals. The loss of apoptotic mechanisms often results in abridged response to cancer therapy. As such, alternate or combinatorial approaches that kill cancer cells and induce tumor regression are being actively pursued by researchers and physicians.

Especially difficult to treat are those cancers which are hormonally related and/or are metastatic cancers. These cancers include, e.g., prostate cancer, breast cancer and lung cancer. Melanoma is also difficult to treat and has a low survival rate relative to many other cancers.

An essential feature of anticancer strategies is the selective action against cancer cells, with little or no damage inflicted in normal cells. Nonetheless, side effects of cancer therapies are often severe. They include nausea, vomiting, pain, poor appetite, wasting, cachexia, diarrhea, burning in the stomach, stress, planter warts, nerve death-neuropathy, radiation burns, fatigue, constipation, anemia, anxiety, weakened immune system, dry skin, bone marrow suppression and hair loss. As such the identification of molecules that can specifically target tumor cells, with minimal or no adverse effects to normal cells constitutes a significant area of cancer research. Such molecules with selective action against tumor cells are valuable not only for their therapeutic potential; but also for their potential applications as tools for dissection of fundamental differences between normal and cancer cells. Thus, treatment methods that specifically target certain types of hormonally linked cancers would be extremely useful. Additionally, treatment methods that target cancers located in highly vascularized tissues such as for example lung, kidney, liver, or blood, and methods that target difficult to treat cancers, such as for example melanoma, would also be highly beneficial.

BRIEF DESCRIPTION OF THE INVENTION

The tumor suppressor Par-4 (prostate apoptosis response-4) induces apoptotic cell death specifically in cancer cells but not in normal cells. This cancer-selective action is attributed to its centrally located SAC domain (El-Guendy et al. (2003) "Identification of a unique core domain of Par-4 sufficient for selective apoptosis-induction in cancer cells." *Mol. Cell. Biol.* 23, 5516-5525).

The Par-4 protein has not only an intracellular function, but it is also secreted by both normal and cancer cells (Burikhanov et al. (2009). "The tumor suppressor Par-4 activates an extrinsic pathway for apoptosis" *Cell* 138, 377-388.). Secreted Par-4 binds to its receptor GRP78, which is upregulated on the surface of cancer cells, and induces apoptosis (Burikhanov et al. (2009); Bhattarai, T, and Rangnekar V M (2010) "Cancer-selective apoptotic effects of extracellular and intracellular Par-4" *Oncogene* 29, 3873-3880). The basal level of Par-4 secreted by normal cells is inadequate to induce apoptosis of cancer cells or inhibit the growth of tumors (Burikhanov et al. (2009)). However, elevated levels of extracellular Par-4 produced by injecting recombinant Par-4 in mice, cause inhibition of metastatic lung tumors (Zhao et al. (2011) "Systemic Par-4 inhibits metastatic tumor growth". *Cancer Biol Ther.* 12, 152-157).

There are several non-FDA approved small molecules, such as Nutlin-3a, PS-1145, and Arylquin-1 (INV13/1947) that can increase secretion of Par-4 from normal cells in mice and the sera from these mice induced ex vivo apoptosis in cancer cell cultures (Burikhanov et al. (2014) "Paracrine apoptotic effect of p53 mediated by tumor suppressor Par-4". *Cell Reports* 6, 271-277; and Burikhanov et al., "Arylquin-1 targets vimentin to trigger Par-4 secretion for tumor cell apoptosis" *Nature Chem Biol.* 10, 924-926 (2014)).

Disclosed herein is the discovery that chloroquine induces Par-4 secretion via the classical secretory pathway that requires activation of p53. Mechanistically, p53 directly induces Rab8b, a GTPase essential for vesicle transport of Par-4 to the plasma membrane prior to secretion.

In particular, described herein is the discovery that the anti-malarial drug, chloroquine, including in various salt forms, induces robust Par-4 production from normal human and mouse cells and can be used to inhibit proliferation and/or metastasis of cancer cells, and to inhibit recurrent tumor formation in subjects in need thereof. The induction of Par-4 by normal cells in response to chloroquine treatment may be enhanced by administering chloroquine with curcumin and/or ibuprofen. Likewise, chloroquine treatment may be used to sensitize cancer cells to ionizing radiation.

Described herein are methods for harnessing the ability of Par-4 secreted from normal cells to induce apoptosis and inhibit tumor growth of cancer cells. In the methods described herein, chloroquine, with or without curcumin and/or ibuprofen, does not require administration of a chemotherapeutic to enhance induction of Par-4 by normal cells and inhibit proliferation and/or metastasis of cancer cells or to inhibit recurrent tumor formation. Thus, in an aspect of this invention, chloroquine is administered without a chemotherapeutic agent. Also an aspect of this invention is a method for treating a subject having cancer cells that are p53-deficient but nonetheless unexpectedly undergo apoptosis in response to Par-4 exposure, by administering an effective amount of chloroquine to the subject. An effective amount of chloroquine is sufficient to increase Par-4 secretion by normal cells to a level that induces apoptosis of the cancer cells, and/or inhibits proliferation of such cancer cells and/or inhibits metastasis of such cancer cells.

Also an aspect of this invention is a method for treating a subject having cancer cells that are p53-deficient and are resistant to apoptosis induced by Par-4 exposure. The method comprises increasing the amount of Par-4 receptor on such cells, e.g., by administering an effective amount of an NF-kB inhibitor, e.g., PS-1145, and administering an effective amount of chloroquine to the subject. An effective amount of NF-κB inhibitor is an amount sufficient to elevate the level of Par-4 receptor, thereby increasing the cancer cells' responsiveness to apoptosis induced by Par-4. An effective amount of chloroquine is an amount sufficient to increase Par-4 secretion by normal cells to a level that kills the p53-deficient cancer cells, e.g., by inducing apoptosis of the p53-deficient cancer cells, and/or inhibits proliferation of such cancer cells and/or inhibits metastasis of such cancer cells, in the presence of Par-4.

BRIEF DESCRIPTION OF THE DRAWINGS

FIG. 1C is a western blot of serum samples of C57/BL6 mice collected 24 hours after treatment with chloroquine. FIG. 1D is a western blot of pre-operative and post-operative serum samples collected from renal cell carcinoma patients who received hydroxychloroquine ("HCQ") (400 mg daily for 2-weeks) pre-operatively at the University of Pittsburgh, as part of a clinical trial in 2010-2011.

FIG. 2A demonstrates that serum from Par-4$^{+/+}$ mice but not Par-4$^{-/-}$ mice injected with chloroquine showed robust Par-4 secretion relative to serum from vehicle-treated mice.

FIG. 2B demonstrates that serum from chloroquine-treated Par-4$^{+/+}$ mice induced ex vivo apoptosis in H460 cells, and this action of serum was neutralized by the Par-4 (P) or GRP78 (G) antibody but not by the control (C) antibody.

FIG. 2C depicts that A549 cells treated with the NF-κB-inhibitor PS-1145, which elevates Par-4 receptor GRP78 on the cancer cell surface (Burikhanov et al. "Novel mechanism of apoptosis resistance in cancer mediated by extracellular PAR-4". *Cancer Res.* 73: 1011-1019, 2013. PMCID: PMC3549021), were sensitized to apoptosis by Par-4 secreted in CM from MEFs in response to chloroquine treatment.

FIG. 2D demonstrates that the serum from a patient who showed ~3-fold induction of Par-4 following HCQ treatment induces apoptosis in cancer cells PC-3, H460, HOP92, and H1299 relative to the background level apoptosis produced by aliquots of pre-HCQ treatment serum.

FIG. 2E demonstrates that apoptosis of H460 cancer cells by post-treatment serum from RCC4 was neutralized by the Par-4 (P) or GRP78 (G) antibody.

FIG. 2F demonstrates the serum from mice treated with a single dose of CQ but not the serum from control vehicle-treated mice induced ex vivo apoptosis of cancer cells, and this activity was neutralized by the Par-4 (P) or GRP78 (G) antibody.

FIG. 4A depicts response of wild type or p53-null MEFs treated with chloroquine or Nutlin-3a. Robust induction of Par-4 secretion is seen in wild type MEFs but not in p53-null MEFs in response to chloroquine treatment.

FIG. 4B depicts inhibition of NF-κB activity, but not AP1 activity, by chloroquine in normal cells but not in cancer cells.

FIG. 4C depicts chloroquine inhibition of UACA expression in MEF, but not p53 null MEFs, (left panels) and in HELs.

FIG. 4D depicts inhibition of CQ-induced Par-4 expression by BFA.

FIG. 8A depicts CQ induced p53-dependent transcription and upregulation of p53-responsive genes.

FIG. 8B depicts CQ induced upregulation of p53-responsive genes.

FIG. 8C demonstrates CQ does not elevate Par-4 RNA levels.

FIG. 8D demonstrates CQ did not induce p53 or Rab8b, or UACA downregulation in cancer cells.

FIGS. 9A-9D demonstrate that Rab8b is a novel target of p53 critical for Par-4 secretion from normal cells. FIG. 9A demonstrates that Rab8b-null MEF cells, but not Rab8a-null MEF cells, failed to show induction of Par-4 secretion by CQ. FIG. 9B demonstrates that CQ induced Par-4 secretion in Rab8b-null MEFs transiently transfected with mouse Rab8b expression construct or with vector for control. FIG. 9C demonstrates that knocking down Rab8b with siRNAs resulted in inhibition of Par-4 secretion in the CM, as judged by Western blot analysis. FIG. 9D demonstrates that Par-4 secretion is rescued with the reintroduction of GFP-Rab8b into MEFs, after knockdown of endogenous Rab8b with siRNA.

FIG. 10 demonstrates that p53 directly bound to Rab8b and that CQ treatment resulted in increased interaction of p53 with its binding motif in the Rab8b promoter.

DETAILED DESCRIPTION OF THE INVENTION

Figure 1A:
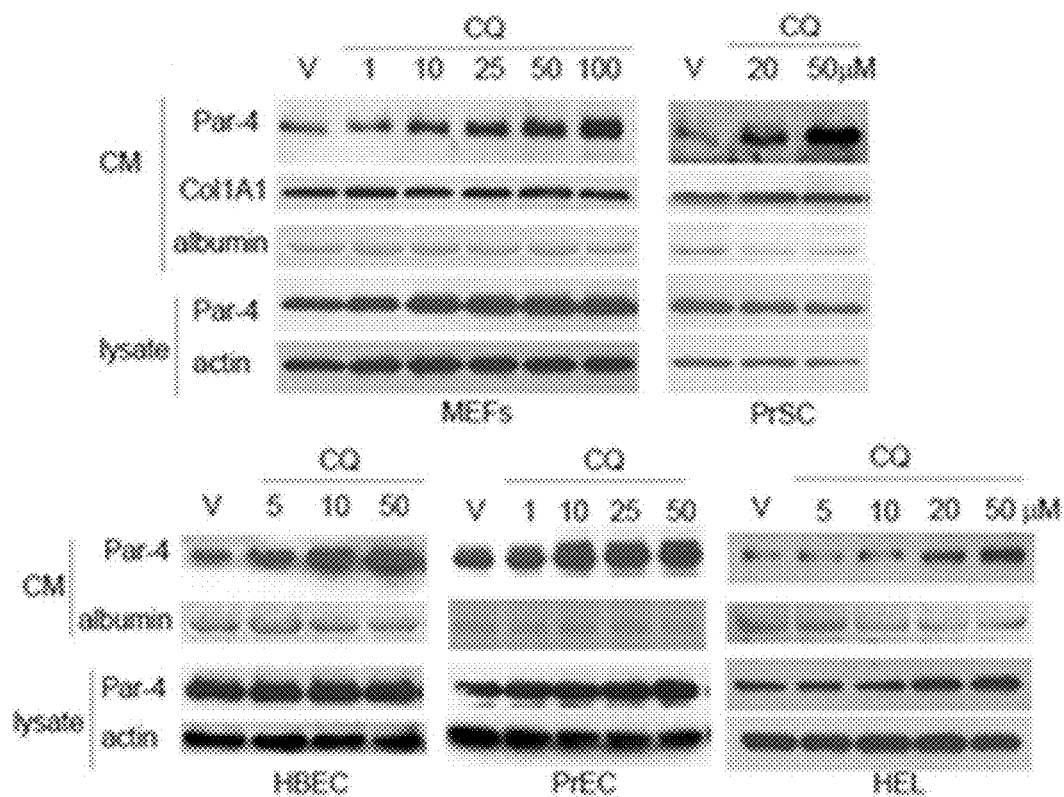
FIGS. 1A-B depict the induction of Par-4 secretion by chloroquine in various normal cell lines (FIG. 1A), but not in prostate or lung cancer cell lines (FIG. 1B). Normal cells lines are mouse embryonic fibroblasts (MEFs, early passage 4 or 5), human primary prostate fibroblast cells (PrSC), human primary prostate epithelial cells (PrEC), human lung embryonic fibroblasts (HEL), human bronchial epithelial cells (HBEC). The human prostate cancer cell lines are androgen-dependent LNCaP cells, and androgen-independent (castration-resistant) C4-2B, DU145 and PC-3 cells and lung cancer cell lines are H460 and A549.

Chloroquine (also known as chloroquine phosphate, and referred to herein as "CP"), chloroquine diphosphate (CQ), and hydroxychloroquine (HCQ or HQ), hereinafter referred to collectively as "chloroquine", have been safely used as an anti-malarial drug for many years. Prior studies have shown that chloroquine may be used to increase the effectiveness of chemotherapy by co-administering chloroquine with a chemotherapeutic agent. Although chloroquine is not currently considered in the clinic for treatment of primary tumors, a number of cell culture and in vivo mouse studies have used chloroquine in combination with standard chemotherapeutic agents for direct action in tumors. Moreover, although it has been reported that chloroquine blocks degradative autophagy (Kimura et al. (2013) "Chloroquine in cancer therapy: a double-edged sword of autophagy" *Cancer Res.* 73:3-7), it has not been reported that chloroquine promotes autophagy-related secretion (Dupont et al. (2011) "Autophagy-based unconventional secretory pathway for extracellular delivery of IL-1" *EMBO J.* 30:4701-11 and; Jiang et al. (2013) "Secretory versus degradative autophagy: unconventional secretion of inflammatory mediators" *J Innate Immun.* 5(5):471-9).

Disclosed herein is the surprising finding that chloroquine, including for example CQ and HCQ, promotes secretion of Par-4 both in vitro and in vivo. Further, treatment of normal cells with CQ or HCQ and curcumin and/or ibuprofen, resulted in a further increase in the levels of Par-4 secreted from normal cells as compared to the levels of Par-4 secreted by cells treated with CQ or HCQ alone.

The results disclosed herein demonstrate that the levels of Par-4 in conditioned medium from cell cultures treated with CQ or HCQ, and the levels of Par-4 in the serum of patients treated with CQ or HCQ cause robust apoptosis of cancer cells, e.g., lung and prostate cancer cells. The enhanced levels of Par-4 induced by CQ or HCQ treatment, with or without curcumin and/or ibuprofen, are useful for inhibiting the growth and/or recurrence of lung and prostate tumors, and for inhibiting tumor metastasis, e.g., brain metastasis of lung tumors, or bone and lung metastasis of prostate tumors.

An aspect of the invention described herein is a method for treating a subject in need thereof with chloroquine (e.g., CP, CQ, and/or HCQ), or a salt or a prodrug thereof, and other agents that promote Par-4 production by normal cells, to increase apoptosis of cancer cells and to reduce the metastasis and proliferation and/or survival of cancer cells. Another aspect of this invention is a method for treating a subject in need thereof with a combination of chloroquine, or a salt or a prodrug thereof, with curcumin and/or ibuprofen to elevate Par-4 production by normal cells, to increase apoptosis of cancer cells, to reduce the metastasis and proliferation and/or survival of cancer cells.

In an aspect, the present invention includes methods of treating cancer cells that respond to exogenously added Par-4 but are nonresponsive to chloroquine, or a salt or prodrug of chloroquine (ie, cancer cells nonresponsive to chloroquine will not produce their own Par-4 in response to chloroquine). The method comprises contacting a population of cells comprising cancer cells that are nonresponsive to chloroquine, or a salt or prodrug thereof, and normal cells that are responsive to chloroquine, or a salt or prodrug thereof, with an effective amount of chloroquine, or salt or prodrug thereof, wherein treatment with the effective amount of chloroquine, or salt or prodrug thereof, kills cancer cells, inhibits cancer cell proliferation, cancer cell metastasis, and/or recurrence of one or more tumors.

In a preferred aspect, cancer cells that are nonresponsive to chloroquine, or salt or prodrug thereof, are those cancer cells where expression of Par-4 by those cancer cells is not increased in response to exposure to chloroquine, or a salt or prodrug thereof. In a further preferred aspect, normal cells that are responsive to chloroquine, or salt or prodrug thereof, are those normal cells where expression of Par-4 by those normal cells is increased in response to exposure to chloroquine or a salt or prodrug thereof. In the context of the present invention, a normal cell refers to a non-malignant cell.

By the present invention, a salt or prodrug of chloroquine may include any salt or prodrug with pharmacological activity in vitro and/or in vivo that is similar to the pharmacological activity of CP, CQ, or HCQ as discussed herein. Such salts and prodrugs will be readily apparent to the skilled artisan and can be readily prepared by the skilled artisan based on knowledge in the art.

The present invention includes a method of killing cancer cells, e.g., by inducing apoptosis, or inhibiting cancer cell proliferation, cancer cell metastasis, and/or recurrence of tumors in a subject comprising administering an effective amount of an agent to a subject in need of treatment for sufficient time to increase prostate apoptosis responsive 4 (Par-4) secretion from normal cells in the subject, wherein the agent is chloroquine phosphate, chloroquine diphosphate, hydroxychloroquine, or a salt or a prodrug thereof, and wherein the agent is not administered with a chemotherapeutic.

In the methods of this invention, the chloroquine, or salt or prodrug thereof, is administered to a subject in need thereof in an effective amount, e.g., an amount sufficient to increase Par-4 expression and/or secretion level above the level of Par-4 expressed, secreted, or both by a normal cell prior to administration of the chloroquine or salt or prodrug thereof. In another aspect, an effective amount of chloroquine, or salt or prodrug thereof, is an amount sufficient to increase apoptosis of cancer cells, and/or reduce proliferation and/or reduce metastasis of cancer cells in the subject. Preferably, the chloroquine or salt or prodrug thereof is administered in an amount that induces apoptosis in cancer cells while having little or no detrimental effect on kidney function in the subject.

By way of non-limiting example, an effective amount of chloroquine contacted with cells may include for example about 200 nM to about 10004, about 150 nM to about 75 μM, about 100 nM to about 50 μM, about 100 nM to about 40 μM, about 100 nM to about 35 μM, about 100 nM to about 30 μM, about 100 nM to about 25 μM.

In various embodiments, an effective amount of chloroquine is contacted with cells for at least about 2 hours, at least about 5 hours, at least about 10 hours, at least about 16 hours, at least about 18 hours, at least about 20 hours, at least about 24 hours, at least about 2 days, at least about 3 days, at least about 5 days, at least about a week, at least about 2 weeks, or more than 2 weeks.

By way of further non-limiting example, an effective amount of chloroquine administered to a subject in need thereof may include about 50-2000 mg daily, about 100-1500 mg daily, about 150-1200 mg daily, about 200-1200 mg daily, about 100 mg daily, about 200 mg daily, about 300 mg daily, about 400 mg daily, about 500 mg daily, about 750 mg daily, about 1000 mg daily, about 1200 mg daily or more than about 1200 mg daily.

In various embodiments, an effective amount of chloroquine is administered to a subject in need thereof for 1 day, for 2 days, for 5 days, for about 1 week, for about 2 weeks, for at least about 1 month, for at least about 2 months, for at least about 3 months, for at least about 6 months, for at least about 8 months, for at least about 1 year, or for more than 1 year. It is understood that the duration of treatment will depend upon the stage of cancer and whether the cancer has gone into remission.

The actual amount encompassed by the term effective amount will depend on the route of administration, the type of subject being treated, and the physical characteristics of the specific subject under consideration, e.g., their age, weight, severity of disease, co-morbidities. These factors and their relationship to determining this amount are well known to skilled practitioners in the medical, and other related arts and one of skill in the art can readily determine the appropriate effective dose of chloroquine to be administered to a subject to achieve the desired levels of Par-4 secretion. Likewise, the dosing schedule may be readily determined by the skilled artisan.

As chloroquine has been used in the art for the treatment of malaria, one of skill in the art could readily modify known pharmaceutical formulations of chloroquine used in the treatment of malaria such that they are suitable for use in the methods described herein.

In some aspects, the chloroquine may be administered in a single dose and may be administered with or without another agent including, e.g curcumin, ibuprofen, ionizing radiation, a chemotherapeutic agent, or any combination thereof. In some aspects of this invention, the chloroquine with or without another agent may be is administered in multiple doses. Dosing may be once, twice, three times, four times, five times, six times, or more than six times per day. In some cases, continuous dosing is achieved and maintained as long as necessary. Dosing may also be formulated for extended release.

The chloroquine and chloroquine salts or prodrugs thereof, with or without curcumin and/or ibuprofen may be administered to the subject by any means currently used in the art, e.g., orally, subcutaneously, intravenously, intramuscularly, parenterally, rectally, etc. For example, the chloroquine or chloroquine salt or prodrug thereof may be administered orally to the subject in any pharmaceutically acceptable form, e.g., in the form of a tablet, a capsule, a syrup, or an elixir, or infused or injected by, e.g., an intraperitoneal or intravenous or intramuscular route, and in an amount sufficient to increase the levels of Par-4 in the subject, preferably to a level that is sufficient to kill the cancer cells, e.g., induce apoptosis in cancer cells, and/or inhibit proliferation and/or inhibit metastasis. Pharmaceutically acceptable forms may also comprise one or more pharmaceutically acceptable carriers, diluents, or excipients. Pharmaceutically acceptable carriers, diluents, or excipients are known in the art such as those described in, for example, Remington's Pharmaceutical Sciences, Mack Publishing Co. (A. R. Gennaro edit. 1985), incorporated herein by reference.

The cancer cells and cancers that are treated may be of any type, including but not limited to, e.g., prostate cancer, breast cancer, skin cancer (e.g., melanoma), lung cancer, and/or any combination thereof. In an embodiment, cancer does not include any type of renal cancer. In a further embodiment, cancer does not include renal cell carcinoma but may include other types of renal cancer, such as for example transitional cell cancer of the renal pelvis (TCC) or Wilms' tumor in children.

The cancer may comprise cancer cells that are hormone responsive or hormone non-responsive or the cancer may be one that is susceptible or refractory to one or more chemotherapeutic treatment. For example, the cancer may be a prostate, or breast cancer, e.g., an androgen independent prostate cancer cells, a breast cancer that expresses no or low levels of Par-4, or a highly aggressive, estrogen receptor-negative, high-grade (grade 3) or basal-like tumor. The cancer may also be a lung cancer, e.g., non-small cell lung cancer, small cell lung cancer and lung carcinoid tumor, that is sensitive to or refractory to treatment with a chemotherapy. The cancer may be a malignant melanoma and may include for example superficial spreading melanoma, nodular melanoma, or lentigno maligna melanoma or desmoplastic melanoma.

In an embodiment of the present invention, a cancer cell or tumor is located in a highly vascularized tissue. In the context of the present invention, a highly vascularized tissue includes any tissue with better than average vascularization. For example, without limitation, highly vascularized tissue includes blood, lung, liver, skin, or kidney. In an embodiment of the present invention, a cancer cell or tumor is located in a highly vascularized tissue that does not include a kidney.

A cancer cell or cancer that is located in a highly vascularized tissue may have originated in that or another highly vascularized tissue or may have traveled to a highly vascularized tissue from any other tissue by metastasis. In an embodiment of the present invention, the cancer cell is p53 deficient. A p53-deficient cancer cell may have a p53-deficient genotype or phenotype. For the purposes described herein a p53-deficient cancer cell has, e.g., a mutation within the p53 gene, e.g., insertion(s), deletion(s) of part or all of the gene, substitution(s) etc. such that no p53 or a mutant p53, e.g., one that does not bind DNA effectively, is produced.

Preferably the chloroquine, or salt or prodrug thereof, is not co-administered with a chemotherapeutic, particularly a chemotherapeutic used in the treatment of prostate or lung cancer, e.g., carmustine, Akt inhibitor MK2206, sulforaphane, or PI103, cisplatin-etoposide, cyclophosphamide, and fluroruracil. As used herein, chemotherapeutics does not include curcumin and/or ibuprofen.

By the methods of the present invention, the chloroquine may optionally be administered with an effective amount of curcumin, ibuprofen or both curcumin and ibuprofen. An effective amount of curcumin and/or ibuprofen for use in the methods described herein is the amount of curcumin and/or ibuprofen administered to the subject in need thereof that is sufficient to increase expression and/or secretion of Par-4 by the normal cells of the subject. Preferably the curcumin and/or ibuprofen are administered to the subject in an amount and for a sufficient time to enhance the production and/or secretion of Par-4 induced by treatment with chloroquine or a chloroquine salt or prodrug thereof alone.

By way of non-limiting example, an effective amount of curcumin contacted with cells may include for example about 0.1-100 µM, about 0.2-50 µM, about 0.5-20 µM, about 1-10 µM, about 1 µM, about 2 µM, about 3 µM, about 4 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 50 µM, about 75 µM, about 100 µM, about 120 µM, about 150 µM, about 180 µM, about 200 µM, about 300 µM, about 400 µM, about 500 µM, about 1000 µM, or more than about 1000 µM.

By way of further non-limiting example, an effective amount of curcumin administered to a subject in need thereof may include, e.g., a daily dose of about 100 mg to about 1500 mg, or about 100 mg to about 1200 mg, or about 500 mg to about 1000 mg, or about 250 to about 500 mg, or about 250 mg to about 1000 mg.

By way of non-limiting example, an effective amount of ibuprofen contacted with cells may include for example about 100-2500 µM, about 200-2000 µM, about 500-1500 µM, about 500-1000 µM, about 500-750 µM, about 750-1000 µM, about 250 µM, about 350 µM, about 500 µM, about 600 µM, about 700 µM, about 750 µM, about 800 µM, about 850 µM, about 1000 µM, about 1250 µM, about 1500 µM, about 1750 µM, about 2000 µM, or more than about 2000 µM.

By way of further non-limiting example, an effective amount of ibuprofen administered to a subject in need thereof may include, e.g., a daily dose of about 200 to about 400 mg/dose every 8 hours, or about 600 mg/day to about 1200 mg/day, about 1000-about 3200 mg/day, about 1500-about 3000 mg/day, about 1800-about 2500 mg/day, about 1200-about 2000 mg/day, about 2500-about 3200 mg/day, about 400 mg/day, about 600 mg/day, about 800 mg/day, about 1000 mg/day, about 1200 mg/day, about 1400 mg/day, about 1600 mg/day, about 1800 mg/day, about 2000 mg/day, about 2200 mg/day, about 2400 mg/day, about 2600 mg/day, about 2800 mg/day, about 3000 mg/day, or about 3200 mg/day.

An effective amount of chloroquine and curcumin or ibuprofen, or both, are contacted with cells for sufficient time to increase and/or maintain an elevated level of secreted Par-4 from the cells. In various embodiments, an effective amount of chloroquine and curcumin or ibuprofen, or both, are contacted with cells for at least about 2 hours, at least about 5 hours, at least about 10 hours, at least about 16 hours, at least about 18 hours, at least about 20 hours, at least about 24 hours, at least about 2 days, at least about 3 days, at least about 5 days, at least about a week, at least about 2 weeks, or more than 2 weeks.

An effective amount of chloroquine with curcumin or ibuprofen, or both, is administered to a subject in need thereof for sufficient time to increase and/or maintain an elevated level of secreted Par-4 in the subject. In various embodiments, the chloroquine and curcumin or ibuprofen, or both, may be administered to the subject in need thereof for 1 day, for 2 days, for 5 days, for about 1 week, for about 2 weeks, for at least about 1 month, for at least about 2 months, for at least about 3 months, for at least about 6 months, for at least about 8 months, for at least about 1 year, or for more than 1 year.

The curcumin and/or ibuprofen may be co-administered to the subject with the chloroquine or chloroquine salt or prodrug thereof. For the purposes of this invention, co-administered or co-administering or co-administration refers to the administration of two or more agents or therapies (e.g., radiation therapy) to a subject in any manner in which the pharmacological effects of the agents or therapies are manifest in the subject at the same time. Co-administration does not require that the agents or therapies be administered in a single pharmaceutical composition, in the same dosage form, at the same time, or by the same route of administration. The effects of the agents or therapies need not manifest themselves at the same time. The effects need only be overlapping for a period of time and need not be coextensive.

The methods of the present invention may also include treatment with chloroquine and an effective amount of ionizing radiation. Ionizing radiation has been used in the treatment of a variety of cancers, including melanoma (Khan et al. Onco Targets Ther. 2011; 4: 137-148). An effective amount of ionizing radiation may include any amount that is sufficient to kill cancer cells, inhibit cancer cell proliferation, cancer cell metastasis, and/or recurrence of one or more tumors. In an embodiment, an effective amount is about 1-5 Gy of radiation, 2-4 Gy of radiation, or about 2 Gy, about 3 Gy, about 4 Gy, or about 5 Gy of radiation. An effective amount of ionizing radiation will be apparent to the skilled artisan, and in a preferred embodiment, is less than the amount of ionizing radiation required to kill cancer cells, inhibit cancer cell proliferation, cancer cell metastasis, and/or recurrence of one or more tumors in the absence of treatment with chloroquine.

An effective amount of chloroquine may be co-administered with the ionizing radiation treatment. Improved effectiveness of the radiation therapy with administration of chloroquine may be manifested as an increase in cancer cell killing, e.g., cancer cell apoptosis, inhibited proliferation of cancer cells, or inhibited metastasis of cancer cells, as compared to similar subjects in need thereof treated with the same amount of ionizing radiation but without chloroquine treatment. The improved effectiveness of the radiation therapy with administration of chloroquine may alternatively or additionally be manifested by achieving cancer cell killing, e.g., cancer cell apoptosis, inhibited proliferation of cancer cells, or inhibited metastasis of cancer cells, with reduced amounts of ionizing radiation than are historically required to achieve such anti-cancer effects. In an embodiment, the effects of chloroquine treatment and ionizing radiation are unexpectedly more than additive.

A subject in need of treatment is a subject who has cancer, a subject who has been treated for a cancer and is in remission or cancer free, or a subject having a recurrent cancer. The cancer may be any cancer, including but not limited to, e.g., prostate, breast, skin (e.g., melanoma), and/or lung cancer, or any cancer disclosed herein. The cancer may be an androgen independent prostate cancer, a breast cancer that expresses no or low levels of Par-4, a breast cancer that is highly aggressive, estrogen receptor-negative, high-grade (grade 3) or basal-like tumor, or a non-small cell lung cancer, a small cell lung cancer, or a lung carcinoid tumor. The cancer may be a melanoma, e.g., superficial spreading melanoma, nodular melanoma, lentigno maligna melanoma, or desmoplastic melanoma. A subject in need of treatment may also include a subject in need of prophylactic treatment, where a subject in need of prophylactic treatment would be, e.g., a subject who does not currently have a cancer but has been determined to be at higher risk of developing a cancer, particularly a prostate, breast, skin, or lung cancer or any cancer described herein, as compared with the risk of the general population of developing that cancer.

Also an aspect of this invention includes methods for reducing the recurrence of a cancer comprising administering chloroquine, or a chloroquine salt or prodrug thereof, preferably without a chemotherapeutic agent, to a subject in need thereof in an amount sufficient to reduce the recurrence of a cancer in the subject. In the methods described herein, the chloroquine or a chloroquine salt or prodrug thereof may be administered to the subject in need thereof in combination with another agent that increases the production and/or secretion of Par-4. In the methods described herein, chloroquine or a chloroquine salt or prodrug thereof may be administered to the subject in need thereof in combination with an effective amount of curcumin and/or ibuprofen.

Another aspect of this invention is a method for prophylactically reducing the risk of a subject developing cancer comprising administering chloroquine, or a chloroquine salt or a prodrug thereof, to a subject in need thereof to elevate Par-4 expression from normal cells to a level that enhances apoptosis of cancer cells. Still another aspect of this invention is a method for prophylactically reducing the risk of a subject developing cancer comprising administering chloroquine, or a salt or prodrug thereof, in combination with curcumin and/or ibuprofen to a subject in need thereof to elevate Par-4 expression from normal cells to a level that enhances apoptosis in cancer cells.

It is understood that the methods of this invention in some embodiments may include a step of selecting a subject in need thereof, by identifying a subject who has a cancer(s) described herein, or who has been treated for such cancer(s) and is in remission or cancer free, or has a recurrent cancer(s), or is in need of prophylactic treatment, and then administering an effective amount of chloroquine with or without an effective amount of curcumin, ibuprofen, or ionizing radiation, or combinations thereof, to such subject as described herein.

EXAMPLES

Example 1

The Results Presented Herein Demonstrate that Chloroquine Induces Secretion of Par-4 from Normal Cells.

Various normal mouse or human cell lines, mouse embryonic fibroblasts (MEFs, early passage 4 or 5), human primary prostate fibroblast cells (PrSC), human bronchial epithelial cells (HBEC), human primary prostate epithelial cells (PrEC), human lung embryonic fibroblasts (HEL), human prostate cancer cell lines, androgen-dependent LNCaP cells, and androgen-independent (castration-resistant) C4-2B, DU145 and PC-3 cells and human lung cancer cell lines H460 and A549 were treated with 1, 10, 20, 25, 50 or 100 µM of chloroquine diphosphate (CQ) or with a vehicle (V) control for 24 h.

The conditioned medium (CM), as well as the whole-cell lysates were subjected to Western blot analysis with the antibodies specific for Par-4, Collagen (Col1A1), albumin, or actin. Col1A1 served as a loading control for protein secretion, as it is generally unchanged in response to the treatments. The samples were also subjected to SDS/PAGE and Coomassie blue staining to determine albumin levels in serum from the CM as another loading control. The results are presented in FIG. 1.

Figure 1B:
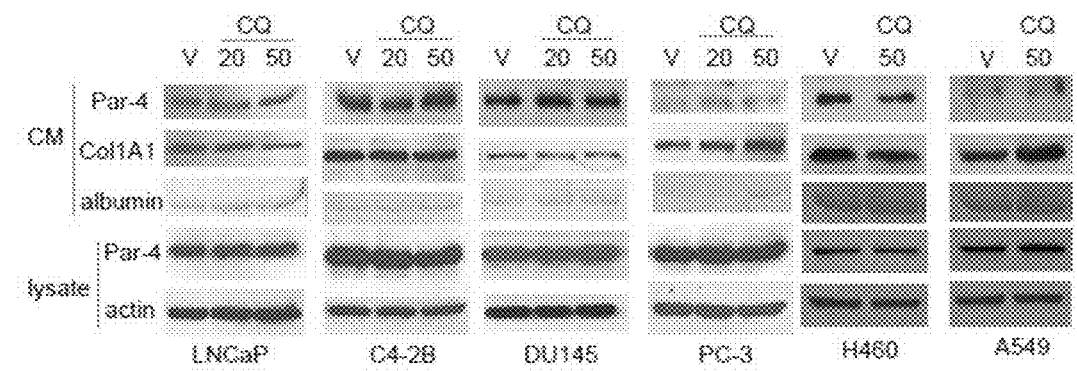

CQ caused dose-dependent secretion of Par-4 in the CM from wild type (p53+/+) MEFs, as well as normal human prostate stromal cells (PrSC) and epithelial cells (PrEC), and normal human lung fibroblasts (HEL) and epithelial cells (HBEC) (FIG. 1A). CQ neither induced Par-4 secretion in prostate cancer cells (LNCaP, C4-2B, DU145 and PC-3) nor in lung cancer cells (H460, A549) (FIG. 1B).

Figure 1C:
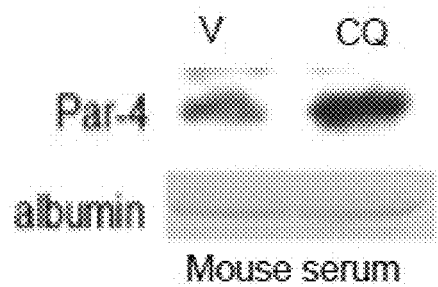
FIGS. 1C-D depict chloroquine-induced systemic expression of Par-4 in mice and in patients.

Immunocompetent mice were injected intraperitoneally with a single dose (50 mg/kg body weight) of CQ or a control vehicle and 24 hours later serum samples were collected and tested for systemic levels of Par-4. Relative to vehicle treatment, CQ induced robust elevation of Par-4 in mouse serum (FIG. 1C).

Figure 1D:
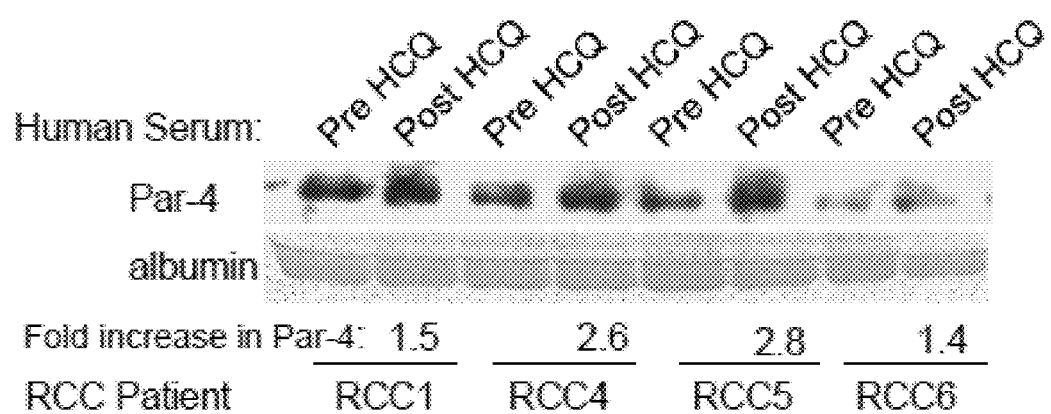

Serum samples were collected from renal cell carcinoma patients who were given safe oral doses (400 mg daily for 2-weeks) of HCQ pre-operatively at the University of Pittsburgh, as part of a clinical trial in 2010-2011. Pre-HCQ treatment and post-HCQ treatment serum samples were collected and frozen. In 2013-2014, they were processed by Western blot analysis. Patients who were taking HCQ prior to surgery showed elevated levels of Par-4 relative to pre-treatment levels (FIG. 1D).

Example 2

The results presented herein demonstrate CQ-inducible Par-4 secretion in CM of normal cells causes apoptosis in cancer cell cultures. Furthermore, the results demonstrate that the serum from a renal cell carcinoma patient who showed ~3-fold induction of Par-4 following HCQ treatment also induces ex vivo apoptosis of various normal and cancer cells.

Briefly, MEFs from Par-4$^{-/-}$ or Par-4$^{+/+}$ mice were treated with vehicle (v) or CQ (20 µM) for 24 h, and their CM was transferred to normal (HEL) or p53-wild type lung cancer cells (H460 and A549), p53-deficient cancer lung cancer cells (HOP92 and H1299), and p53-deficient prostate cancer cells (PC-3 and DU145). After 24 h, the cells were subjected to immunocytochemistry (ICC) for active caspase-3 and apoptotic cells were scored under a fluorescent microscope. The results are depicted in FIGS. 2A-F. An asterisk (*) indicates statistical significance (P<0.001) by the Student's t-test.

Figure 2A:
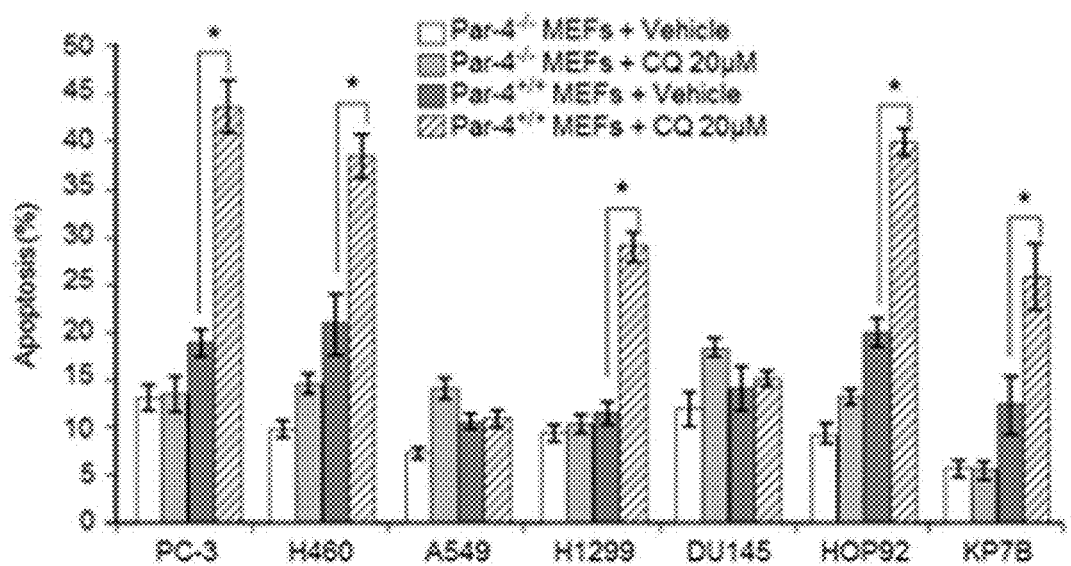
FIGS. 2A-F demonstrate apoptosis in cancer cell cultures by chloroquine-inducible Par-4 secretion in conditioned medium (CM) of normal cells. Cancer cells are p53-wild type lung cancer cells H460 and A549, p53-deficient lung cancer cells (HOP92 and H1299), and p53-deficient prostate cancer cells (PC-3 and DU145). Normal cells (HEL). An asterisk (*) indicates statistical significance (P<0.001) by the Student's t-test. A549 and DU145 cells lack cell surface receptors, and therefore served as an internal control for resistance to the apoptotic action of Par-4.

Prostate cancer cells PC-3, and lung cancer cells H460, H1299, HOP92, KP7B cells, but not normal HEL cells were sensitive to apoptosis when co-cultured with Par-4$^{+/+}$ MEFs, but not Par-4$^{-/-}$ MEFs, treated with CQ. Prostate cancer cells DU145 or lung cancer cells A549 that are resistant to apoptosis by Par-4 were, as expected, resistant to apoptosis by the Par-4 secreted from CQ treated Par-4+/+ MEFs and served as an internal control (FIG. 2A).

Figure 2B:
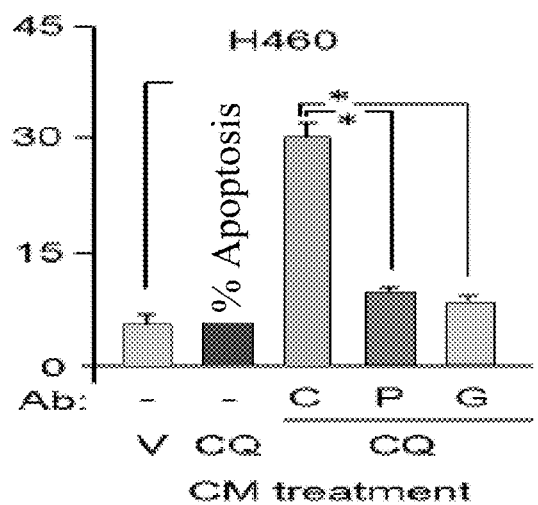

Cancer cell apoptosis was also induced by the CM of Par-4$^{+/+}$ MEFs treated with CQ, and the apoptotic activity of the CM was inhibited by the Par-4 antibody (which neutralizes Par-4 in the CM) or by the GRP78 antibody, which is expected to inhibit binding of Par-4 to GRP78 on the cancer cell surface (FIG. 2B).

Figure 2C:
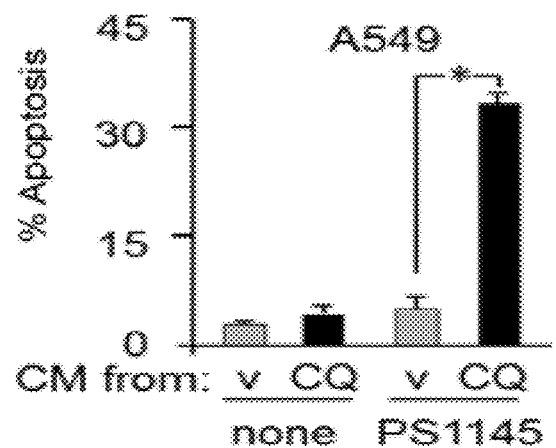

Aliquots of CM from wild type MEFs treated with CQ were incubated with A549 cells pretreated with PS-1145 (10 µM) or vehicle (v). After 24 h, the cells were scored for apoptosis. A549 cells treated with the NF-κB-inhibitor PS-1145, which elevates Par-4 receptor GRP78 on the cancer cell surface (Burikhanov et al. "Novel mechanism of apoptosis resistance in cancer mediated by extracellular PAR-4". *Cancer Res.* 73: 1011-1019, 2013. PMCID: PMC3549021), were sensitized to apoptosis by the Par-4 secreted in the CM from MEFs in response to CQ treatment (FIG. 2C).

Figure 2D:
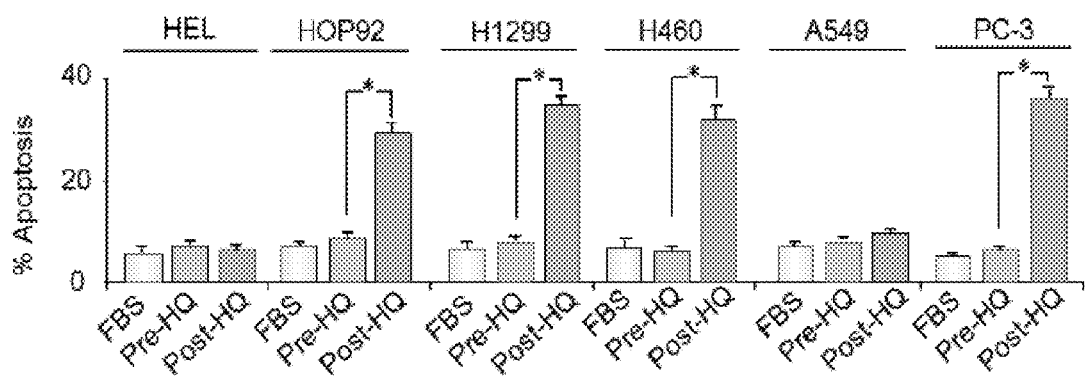
Figure 2E:
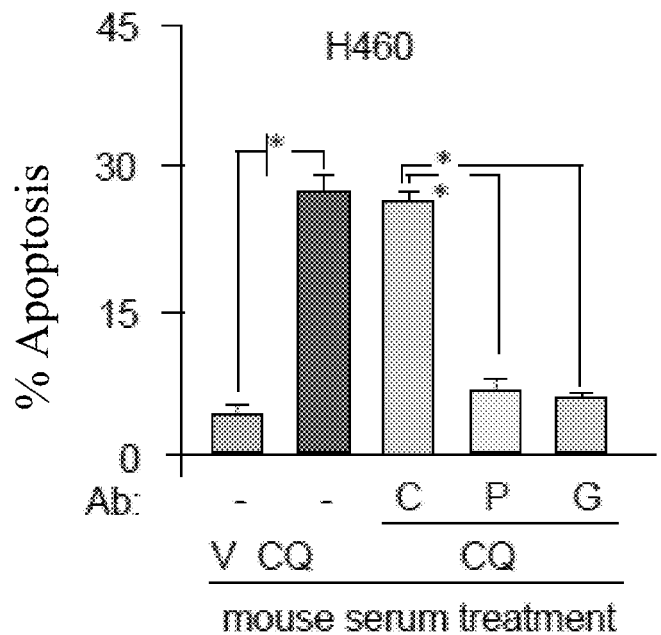

The serum from a renal cell carcinoma patient who showed ~3-fold induction of Par-4 following HCQ treatment (400 mg daily dose of HCQ for 2 weeks) was also assayed for induction of ex vivo apoptosis of various normal and cancer cells. Aliquots of pre-HCQ or post-HCQ treatment serum samples from the patient were transferred to cancer cell cultures (20% final concentration). After 24 h, the cells were scored for apoptosis by ICC for active caspase-3. Fetal bovine serum (FBS, 10%) was used as an additional control. An asterisk (*) indicates statistical significance (P<0.001) by the Student's t-test. The cancer cells, PC-3, H460, HOP92, and H1299, underwent apoptosis with aliquots of post-HCQ treatment serum relative to the background apoptosis level produced by aliquots of pre-HCQ treatment serum (FIG. 2D). Importantly, apoptosis of cancer cells by post-treatment serum from the patient was neutralized by the Par-4 antibody (P) or GRP78 antibody (G), but not by control antibody (C) (FIG. 2E).

Figure 2F:
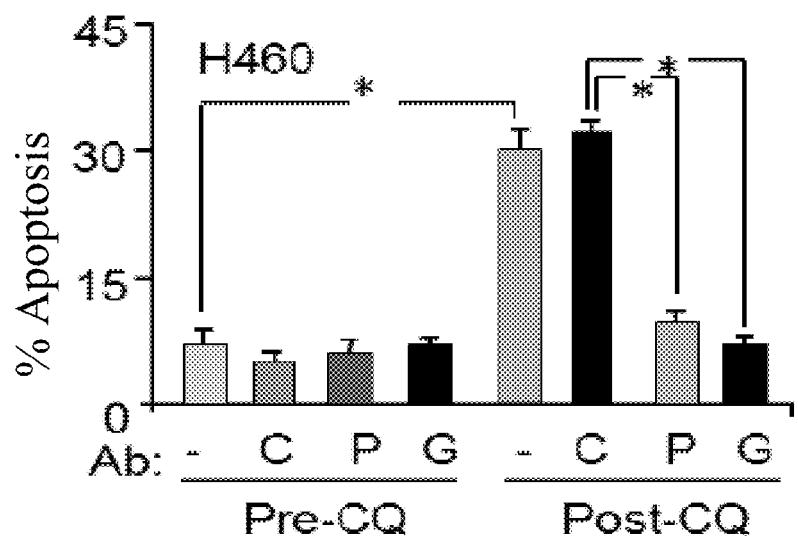

Moreover, the serum from mice treated with a single dose of CQ but not the serum from control vehicle-treated mice induced ex vivo apoptosis of cancer cells, and this activity was neutralized by the Par-4 antibody or GRP78 antibody (FIG. 2F). Together, these findings indicate that CQ-induced Par-4 expression levels, in the CM of cell cultures or in the serum of mice, are adequate to trigger apoptosis of cancer cells.

Example 3

The results presented herein demonstrate that CQ induces tumor growth inhibition by a Par-4-dependent mechanism. The results also demonstrate that Par-4 in serum from CQ-treated mice induces ex vivo apoptosis in LLC1 cells.

Figure 3A:
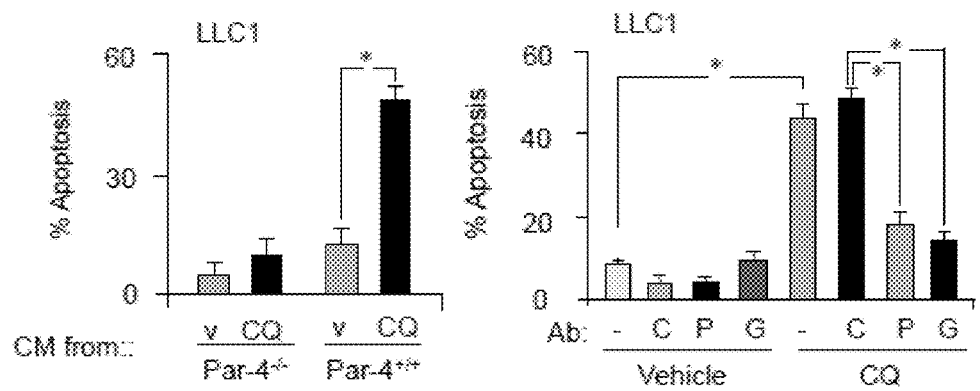
FIG. 3A depicts the apoptotic effects of CM from Par-4$^{+/+}$ MEFs but not with Par-MEFs treated with chloroquine on LLC1 cells and this apoptotic activity in the CM was inhibited by the Par-4 (P) antibody or GRP78 (G) antibody.

Aliquots of culture media (CM) from Par-4$^{-/-}$ or Par-4$^{+/+}$ MEFs treated with CQ (20 µM) or vehicle (v) were incubated with LLC1 cells for 24 h, and the cells were scored for apoptosis. Moreover, aliquots of CM from wild type MEFs treated with CQ or vehicle were incubated with control (C) antibody (Ab), Par-4 (P) Ab or GRP78 (G) Ab and then transferred to H460 cells. After 24 h, the cells were scored for apoptosis. *P<0.0001 by the Student's t-test. CM from Par-4$^{+/+}$ MEFs but not from Par-4$^{-/-}$ MEFs treated with CQ induced apoptosis of LLC1 cells and this apoptotic activity in the CM was inhibited by the Par-4 (P) Ab or GRP78 (G) Ab (FIG. 3A).

In a model of tumor cell metastasis, LLC1 cells were injected intravenously into Par-4$^{+/+}$ (wild type) or Par-4$^{-/-}$ mice, and then CQ (25 mg/kg body weight) was injected once daily for 5 consecutive days. Tumor growth was examined over a 21-day period.

Figure 3B:
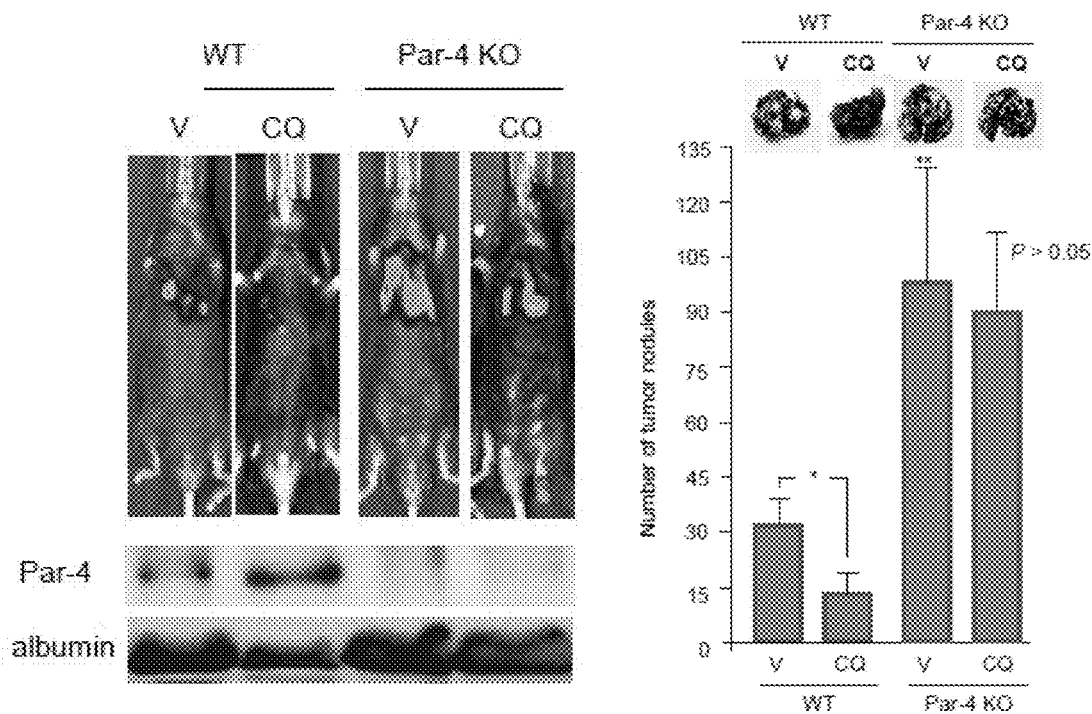
FIG. 3B demonstrates that chloroquine inhibits tumor growth by a Par-4-dependent mechanism.
Figure 3C:
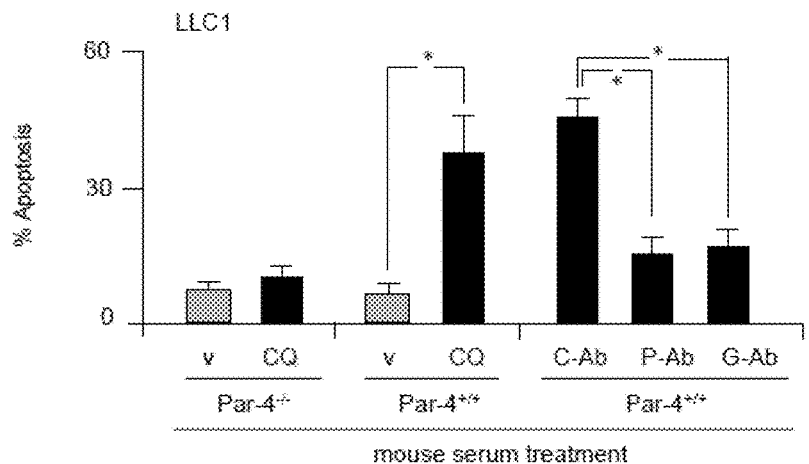
FIG. 3C demonstrates the serum from mice treated with CQ but not the serum from control vehicle treated mice induced ex vivo apoptosis of cancer cells and this apoptotic activity in the CM was inhibited by the Par-4 (P) antibody or GRP78 (G) antibody.

The serum from Par-4$^{+/+}$ mice but not Par-4$^{-/-}$ mice injected with CQ showed robust Par-4 secretion relative to the serum from vehicle-treated mice (FIG. 3B). Importantly, luciferase imaging as well as examination of the mouse tumors indicated strong inhibition (P<0.001 by the Student's t test) of tumor growth in the lungs of CQ-treated Par-4$^{+/+}$ mice. On the other hand, Par-4$^{-/-}$ mice showed a significantly higher number of lung nodules relative to the Par-4$^{+/+}$ mice, and CQ failed to inhibit tumor growth in Par-4$^{-/-}$ mice (FIG. 3B). Moreover, the serum from CQ-treated Par-4$^{+/+}$ mice but not the serum from CQ-treated Par-4$^{-/-}$ mice induced ex vivo apoptosis in LLC1 cells, and this action of the serum was neutralized by the Par-4 or GRP78 antibody but not the control antibody (FIG. 3C). These results demonstrate that basal levels of Par-4 in wild type mice can prevent the establishment and growth of cancer cells, and that Par-4 levels elevated in response to CQ further inhibit tumor growth. Collectively, these findings indicate that Par-4 levels secreted by normal cells in cell culture, mice and patients in response to CQ are adequate to cause ex vivo apoptosis of cancer cells and to inhibit the growth of tumors in mice.

Example 4

The experimental results presented herein demonstrate that CQ induces Par-4 secretion by a p53-dependent mechanism, that CQ inhibits NF-κB activity, but not AP1 activity, and inhibits UACA expression. Furthermore, the results demonstrate that CQ induces Par-4 section by a BFA sensitive mechanism.

Figure 4A:
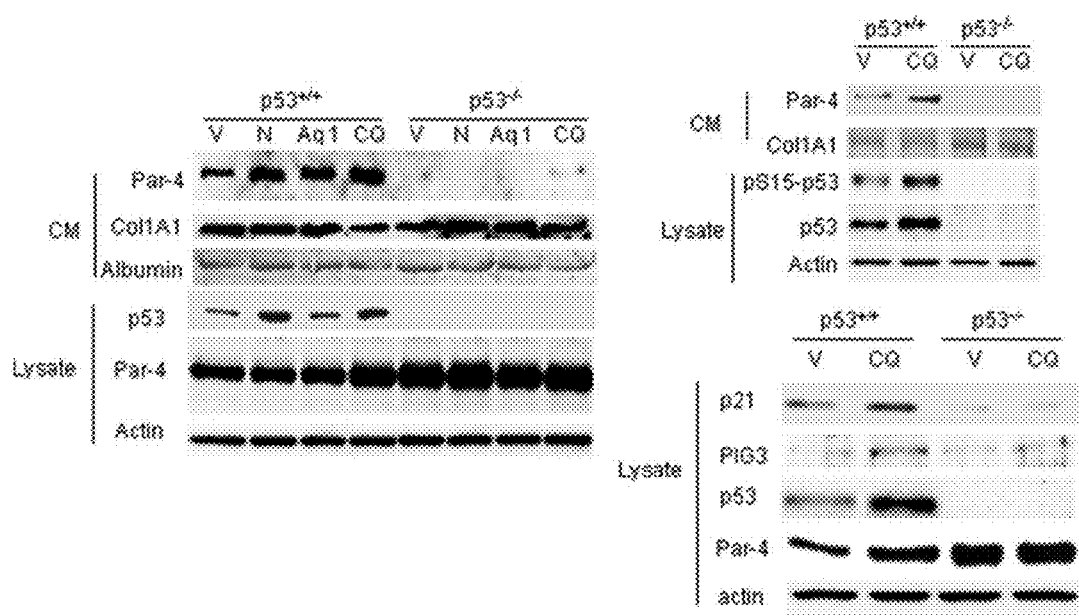
FIGS. 4A-4D demonstrate that chloroquine induces Par-4 secretion by the classical secretory pathway that is dependent on UACA suppression by p53 and by inhibition of NF-κB activity.

Wild type or p53-null MEFs were treated with CQ or Nutlin-3a, which is known to induce Par-4 secretion by a p53-dependent mechanism. CQ caused robust induction of Par-4 secretion in wild type MEFs but not in p53-null MEFs (FIG. 4A). In addition, CQ induced p53 expression in wild type MEFs (FIG. 4A). These data suggested that p53 function was required for Par-4 secretion in response to CQ.

UACA, an inflammation associated protein, binds to Par-4 and sequesters it, thereby preventing Par-4 secretion. UACA expression is inhibited by p53 but is induced by NF-κB-activation. To assess CQ suppression of NF-κB activity and UACA expression, normal and cancer cells were transfected with reporter controls for NF-κB or AP1 and then treated with CQ or vehicle for 24 h. In addition, MEFs were pre-treated with BFA (10 µg/ml) or vehicle for 30 minutes and further treated with CQ (50 µM) or vehicle (V) for 5 h. The CM and lysates were examined by Western blot analysis with the indicated antibodies.

Figure 4B:
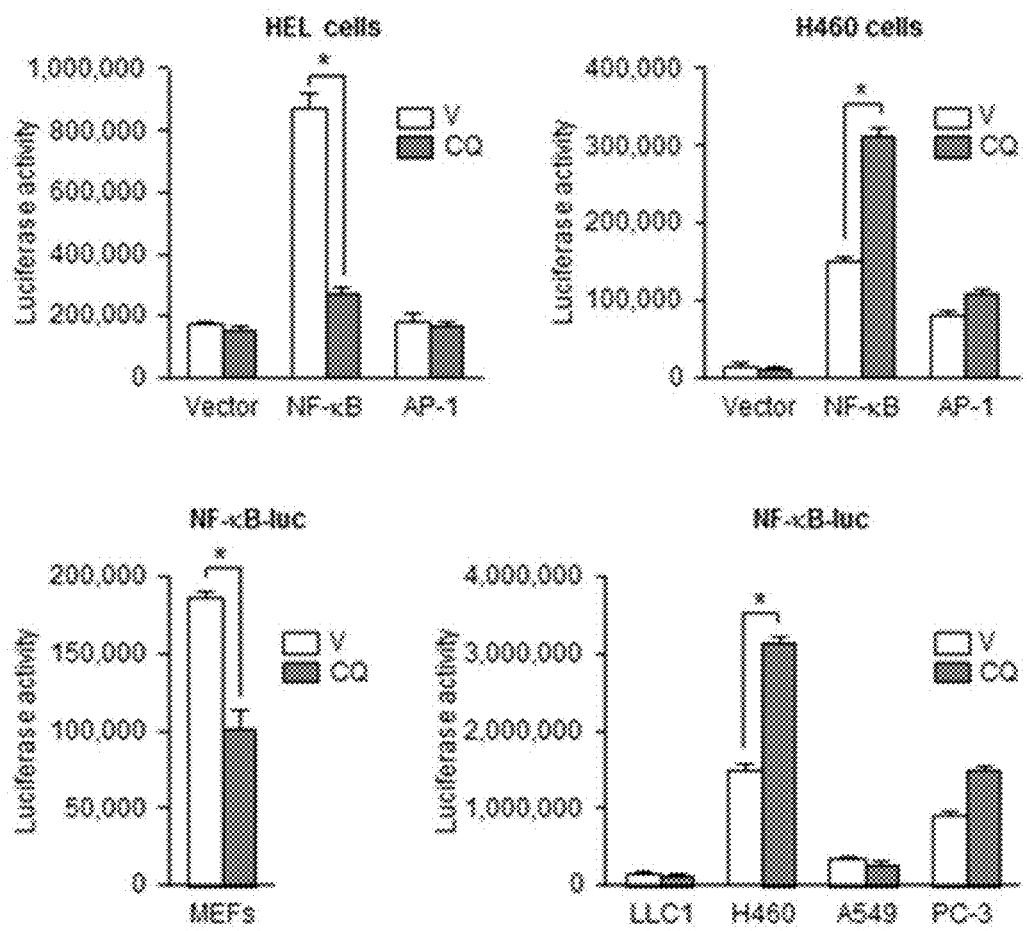
Figure 4C:
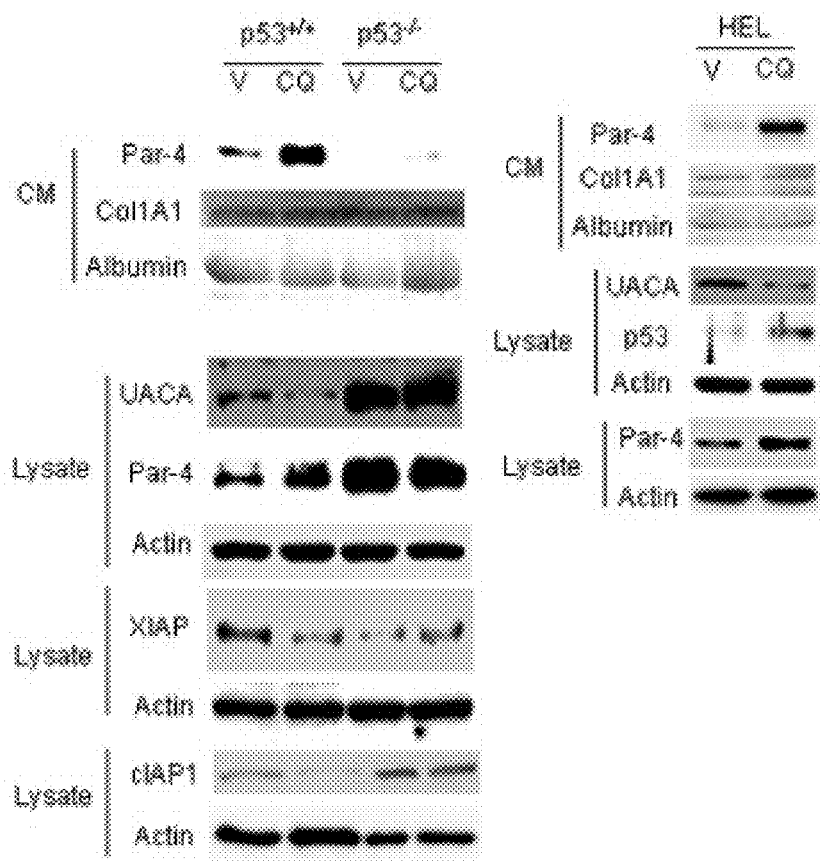
Figure 4D:
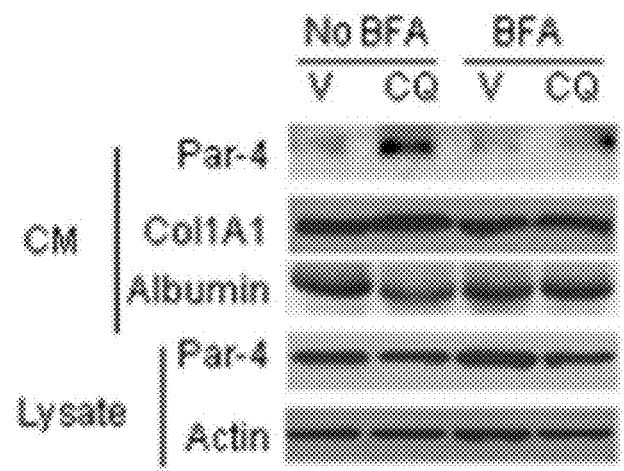

CQ inhibited NF-κB activity, but not AP1 activity, in normal cells but not in cancer cells (FIG. 4B). Moreover, CQ inhibited the expression of UACA in mouse embryonic fibroblasts (MEF), and human embryonic lung fibroblasts (HEL), but not p53 null MEFs (FIG. 4C). CQ-induced Par-4 expression was inhibited by BFA (FIG. 4D). Collectively, these studies indicate that CQ induces Par-4 secretion by the classical secretory pathway that is dependent on UACA suppression by p53 and by inhibition of NF-κB activity.

Example 5

A. Vascularized/Metastatic Lung Cancer Model

To test directly the role of Par-4 secreted in response to CQ, the ability of Par-4 neutralizing antibody to block CQ-induced inhibition of LLC1-derived lung tumor nodules was examined. In an experimental metastasis model, athymic nu/nu mice were injected with 200×10$^5$ LLC1 cells intravenously, and after 24 h, the mice were injected with vehicle or CQ (i.p., 25 mg/kg body weight) once daily for five consecutive days. Animals injected with CQ were also injected within 2 h with either the control IgG or Par-4 polyclonal antibody (20 µg/injection). Each group included 10 mice. After 21 days, the lungs were perfused, stained with India ink (FIG. 6A upper panel) and the tumor nodules were scored (FIG. 6A Lower panel). *P=0.007 by Student's t-test.

Figure 6A:
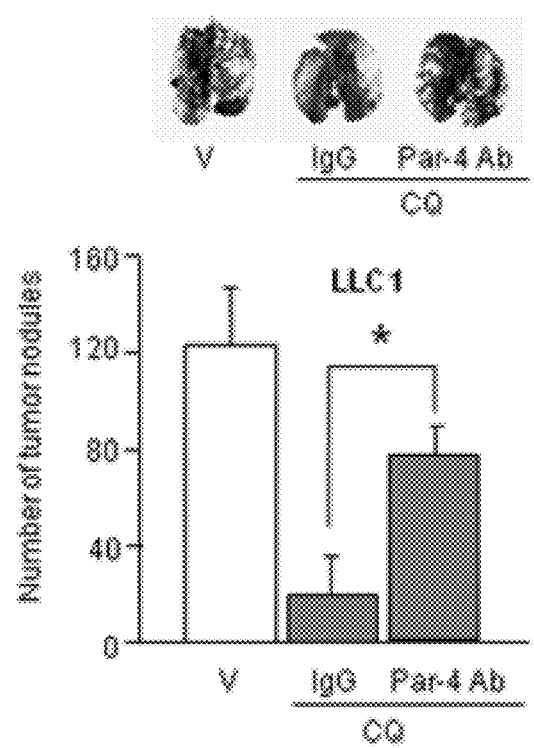
FIG. 6A depicts CQ induced inhibition of tumor nodules in the lungs of nude mice in the presence of control IgG or but not in the presence of Par-4 antibody.

As seen in FIG. 6A, relative to vehicle control, CQ induced >85% inhibition of tumor nodules in the lungs of nude mice in the presence of control IgG, but only ca. 40% inhibition of lung tumor nodules in the presence of Par-4 antibody. These results indicated that CQ-inducible secretion of Par-4 plays a significant role in inhibition of lung tumor nodules in the experimental metastasis model.

B. Non-Vascularized Cancer Model

Figure 6B:
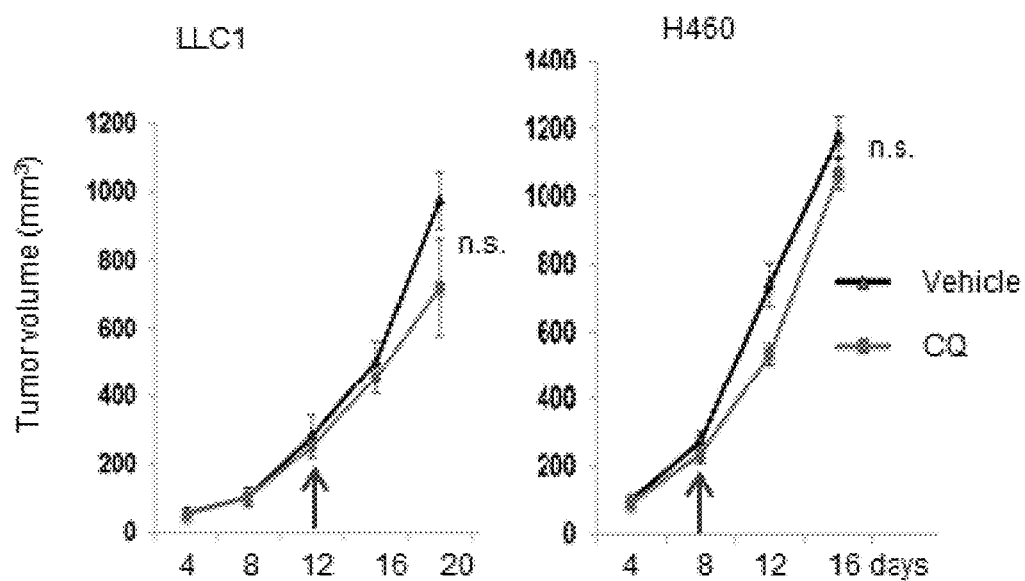
FIG. 6B demonstrates CQ does not significantly inhibit the growth of subcutaneous bulky tumors.

To determine whether CQ inhibits the growth of tumors in tissue that is not highly vascularized, $4 \times 10^5$ H460 or LLC1 cells were injected subcutaneously in nude (nu/nu) mice to generate tumors in the flanks. When the tumors had grown to ca. 200 mm$^3$ volume (indicated by arrow), the mice (10 per group) were injected IP with CQ (25 mg/kg body weight) or vehicle once daily throughout the experiment, and tumor growth was measured with calipers over period of the experiment to calculate tumor volume. In contrast to Example 5A, yet consistent with the findings of Xia et al. (2014) Sci Trans Med 6: 161-182, CQ failed to inhibit the growth of LLC1- or H460-derived tumor xenografts in the flanks of mice (FIG. 6B). Without wishing to be bound by theory, the lack of response may be due to the inability of Par-4 and/or CQ to reach the tumor microenvironment owing to inadequate neovascularization in the subcutaneous tumors.

Collectively, the findings of Examples 5A and 5B indicated that Par-4 levels secreted by normal cell cultures, mice and patients in response to CQ were adequate to cause ex vivo apoptosis of cancer cells and to inhibit the growth of metastatic lung tumor nodules in mice.

Example 6

Figure 7A:
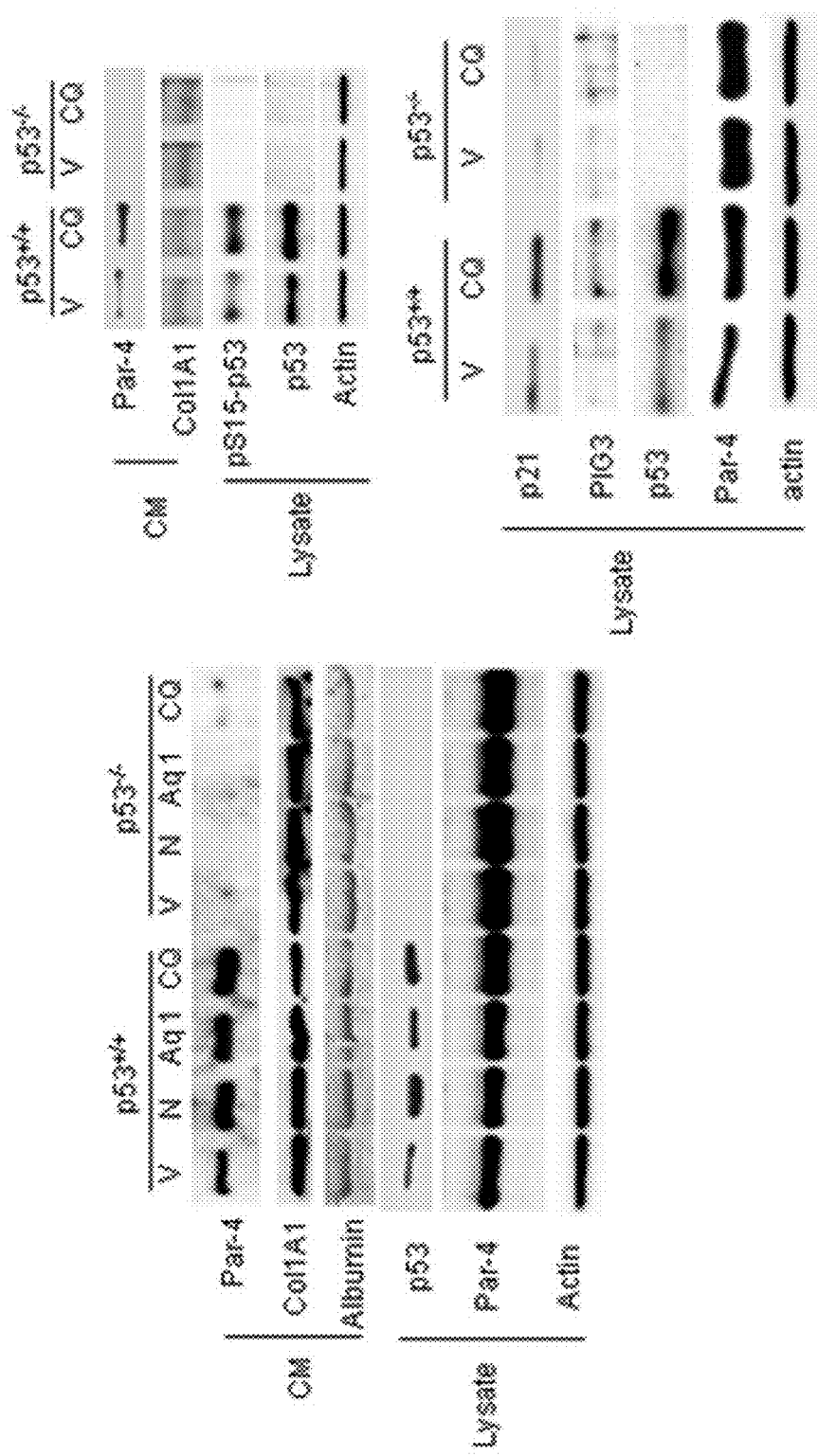
FIG. 7A depicts CQ induced Par-4 secretion by a p53-dependent mechanism. P53+/+ or p53-/- MEFs were treated with CQ (25 µM), Arylquin-1 (500 µM), Nutlin-3a (10 µM) or vehicle (V) for 24 h and the CM and lysates were examined by Western blot analysis with the indicated antibodies.
Figure 7B:
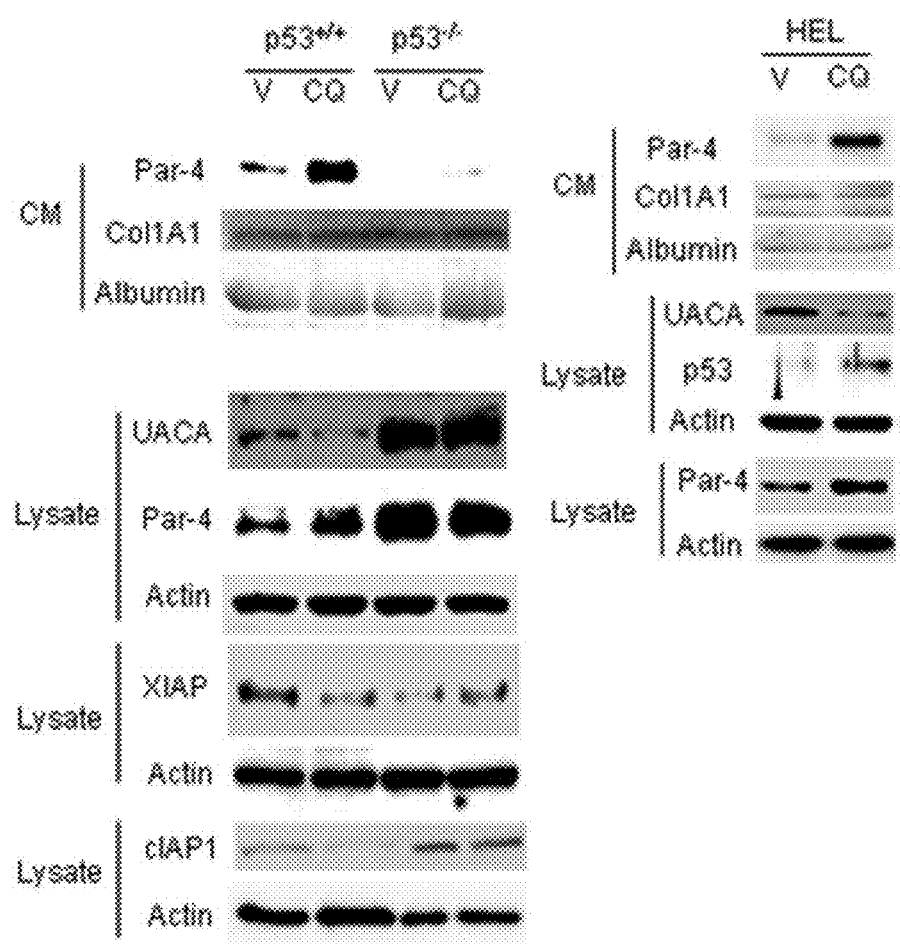
FIG. 7B depicts CQ inhibition of UACA expression. Wild type MEFs and p53-/- MEFs (left panel) or HEL cells (right panel) were treated with CQ (25 µM) or vehicle (V) for 24 h and the CM and lysates were examined by Western blot analysis with the indicated antibodies.

The results presented herein demonstrate induction of Par-4 secretion by CQ required components of the classical secretory pathway Wild type or p53-null MEFs were treated with CQ, Arylquin-1, or Nutlin-3a. Nutlin-3a, an inhibitor of MDM2 binding to p53 (Vassilev et al., 2004 Science 303:844-848), induced Par-4 secretion in a p53-dependent manner (FIG. 7A). Similarly, CQ and Arylquin-1 caused robust induction of Par-4 secretion in wild type MEFs, but not in p53-null MEFs (FIG. 7A). Moreover, CQ induced p53 activation, as judged by the increase in phospho-S15-p53 and total p53 expression in wild type MEFs (FIG. 7A right top panel). Activation of p53 by CQ was accompanied by increased p53-dependent transcription (FIG. 8A), and upregulation of p53-responsive genes p21 and PIG3 in MEFs and normal mouse lung tissues (FIG. 7B and FIG. 8B, respectively). Although CQ caused an increase in total Par-4 protein levels (see FIGS. 1 and 4), it did not induce Par-4 at the RNA level (FIG. 8C), implying that Par-4 protein levels were elevated by CQ induced translational/posttranslational regulation. Collectively, these data suggested that p53 was activated by CQ, and that p53 function was required for induction of Par-4 secretion by CQ, but not for elevation of intracellular Par-4 protein levels. These data are consistent with ChIP data and an observation that the Par-4 (PAWR) gene lacks p53-consensus binding sites for transcriptional regulation by p53 (Burikhanov et al. (2014a)).

It was previously shown that UACA, an inflammation-associated protein, bound to Par-4, sequestered it in the ER, and thereby prevented Par-4 secretion (Burikhanov et al., 2013 Cancer Res 73, 1011-1019). UACA expression was inhibited by p53 but was induced by NF-κB activation. Activation of p53 or inhibition of NF-κB activation promoted Par-4 secretion (Burikhanov et al., 2013).

Testing was done to determine whether CQ suppressed NF-κB activity and UACA expression. Normal (HEL and MEF) or cancer (LLC1, H460, A549, PC-3) cells were co-transfected with luciferase (luc) reporter construct for NF-κB, AP1, or empty luc construct and β-galactosidase expression construct and treated for 18 h with CQ (25 µM) or vehicle (V). Luciferase activity was analyzed in the cell lysates and normalized with respect to the corresponding β-galactosidase activity. *P<0.001 by the Student's t-test. (FIG. 4B). Moreover, CQ inhibited the expression of UACA and NF-κB-regulated genes cIAP1 and XIAP in a p53-dependent manner (FIG. 7B).

By contrast, in cancer cells that failed to show induced Par-4 secretion in response to CQ, CQ neither induced p53 nor did it inhibit NF-κB activity (FIG. 4B), and CQ consistently failed to downregulate UACA (FIG. 8D). Collectively, these studies indicated that similar to our findings with Nutlin-3a (Burikhanov et al., 2014a), CQ-induced Par-4 secretion by the classical secretory pathway that is dependent on UACA suppression by p53 and by inhibition of NF-κB activity.

Example 7

The results presented herein demonstrate Rab8b is a novel target of p53 critical for Par-4 secretion from normal cells.

Figure 9C:
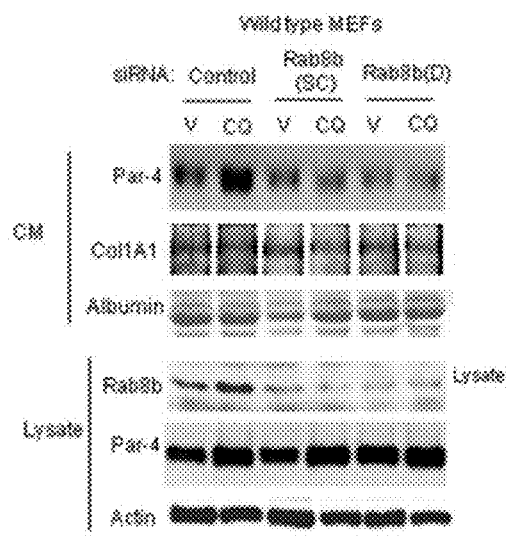
Figure 9D:
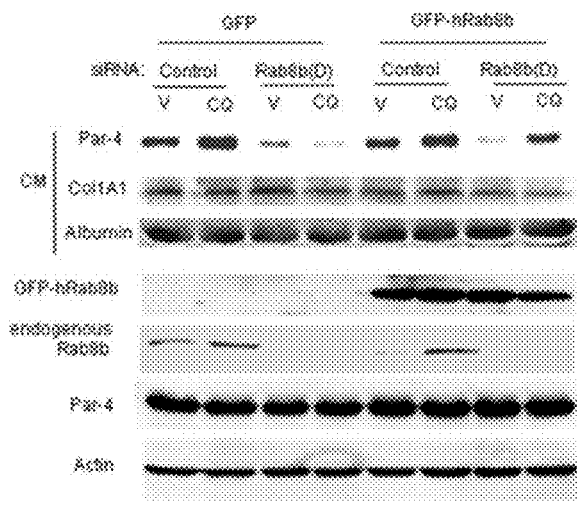

Testing was performed to determine whether the expression of Rab genes containing putative p53 binding sites in their promoter region were essential for Par-4 secretion. These studies indicated that Rab8b-null MEF cells, but not Rab8a-null MEF cells, failed to show induction of Par-4 secretion by CQ (FIG. 9A). CQ-induced Rab8b expression but not Rab8a expression in wild type MEFs (FIG. 9A). CQ also induced Rab8b in normal human cells but not in cancer cells (FIG. 9D). It was determined that Rab8b-null MEF cells were not deficient in p53 induction in response to CQ. Moreover, the effect of transiently transfecting Rab8b-null MEFs with mouse Rab8b expression construct or vector for control was assayed and it was noted that CQ induced Par-4 secretion in Rab8b reconstituted cells (FIG. 9B). Knocking down Rab8b with siRNAs resulted in inhibition of Par-4 secretion in the CM, as judged by Western blot analysis (FIG. 9C), and the reintroduction of GFP-Rab8b into MEFs, after knockdown of endogenous Rab8b with siRNA, rescued Par-4 secretion (FIG. 9D).

Figure 10A:
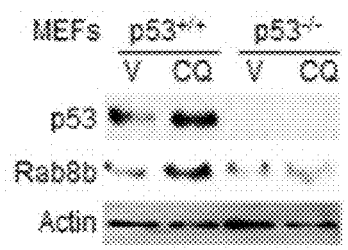
FIG. 10A depicts CQ induction Rab8b protein and mRNA levels in a p53-dependent manner.
Figure 10A:
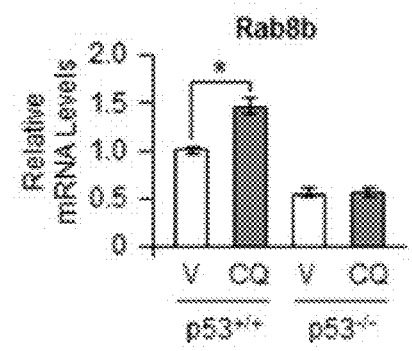

The guardian of the genome, p53 binds to a consensus motif 5'-PuPuPuC4(A/T)(A/T)G7PyPyPy [0-13] PuPuPuC4 (A/T)(A/T)G7PyPyPy-3'(SEQ ID NO: 1) (where purines at 4 and 7 position are critical) in the promoter of genes that it transcriptionally regulates (El-Deiry et al., 1992 Nat Genet 1:45-49). Putative p53-binding sites 5'-GGGGCACGC-CCGAGGCTCCCC-3' SEQ ID NO: 2 on human chromosome 15 (corresponding to nucleotides at position 63481874-63481894) and 5'-GGAGAGCCGCGGGCGT-GCCT-3' SEQ ID NO: 3 on mouse chromosome 9 (corresponding to nucleotides at position 66767671 to 66767690) were noted in the promoter regions upstream of the transcription start site of human and mouse Rab8b, respectively (http://www.sabiosciences.com/chipqpersearch.php). CQ enhanced Rab8b protein levels in p53 wild type cells but not in p53-null cells, and quantitative, real-time PCR studies indicated that CQ induced Rab8b mRNA in a p53-dependent manner (FIG. 10A).

Figure 10B:
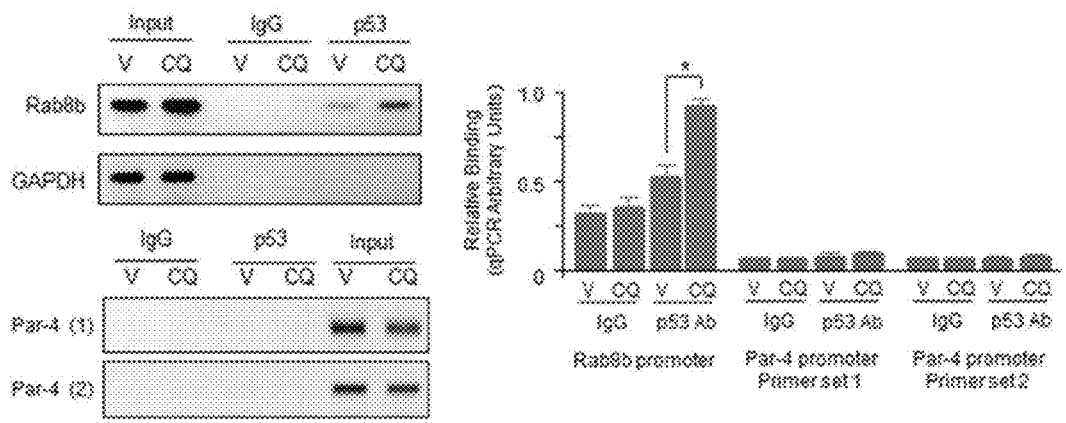
FIG. 10B demonstrates P53 directly binds to its consensus binding site in the Rab8b promoter.

To determine if p53 directly binds to this consensus binding motif within the Rab8b promoter in order to induce Rab8b expression, MEF cells were treated with CQ or vehicle and subjected the DNA to chromatin-immunoprecipitation analysis with p53 antibody (Ab) or control IgG antibody. As seen in FIG. 10B, relative to vehicle, treatment with CQ resulted in elevated levels of chromatin immunoprecipitation of the p53-consensus motif in Rab8b. By contrast, either the control IgG antibody used along with primers near the p53 binding site in the Rab8b promoter or the p53 antibody used along with primers corresponding to the region in the GAPDH promoter or Par-4 gene, where p53 was not expected to bind, failed to show chromatin immunoprecipitation (FIG. 10B). These findings indicated that p53 directly bound to Rab8b and that CQ treatment resulted in increased interaction of p53 with its binding motif in the Rab8b promoter.

Figure 10C:
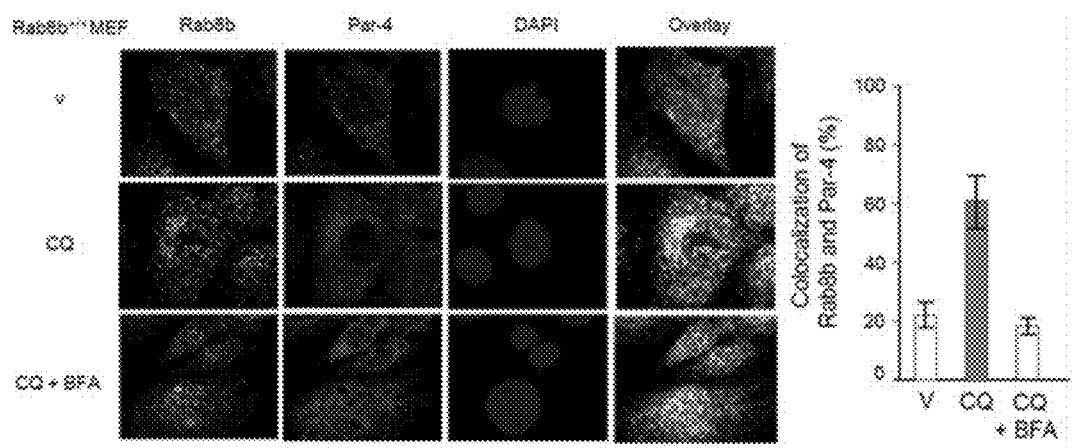
FIG. 10C demonstrates Par-4 co-localized with Rab8b+ vesicles in CQ treated cells.

An immunocytochemical (ICC) analysis was performed to determine the localization of Par-4 in Rab8b coated vesicles. Relative to vehicle treatment, CQ induced an increase in the co-localization of Par-4 with Rab8b containing vesicles, and BFA prevented Par-4 from entering the Rab8b vesicles (FIG. 10C). Together, these findings indicated that the Rab8b gene was induced in a p53-dependent manner and that Rab8b was essential for CQ-induced secretion of Par-4 by the BFA-sensitive post-Golgi pathway to plasma membrane.

Example 8

The results presented herein demonstrate chloroquine sensitizes cancer cells to radiation therapy.

Figure 11A:
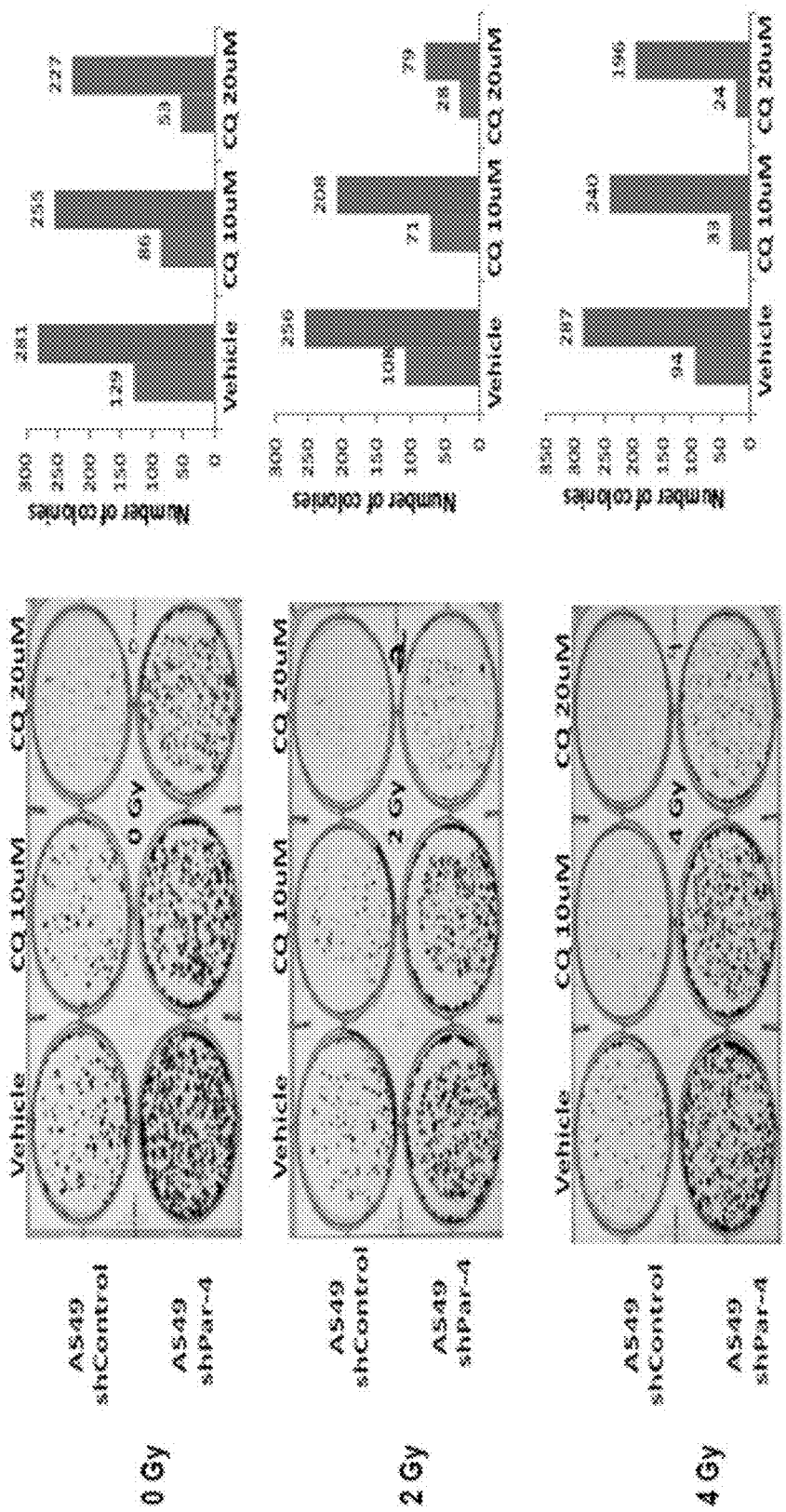
FIG. 11A demonstrates that treatment of A549 lung cancer cells with radiation and CQ has an unexpected greater than additive effect in inhibiting growth and proliferation. The A549 shPar-4 cells showed reduced radiosensitivity and increased growth rate indicating that the action of CQ was dependent on Par-4.
Figure 11B:
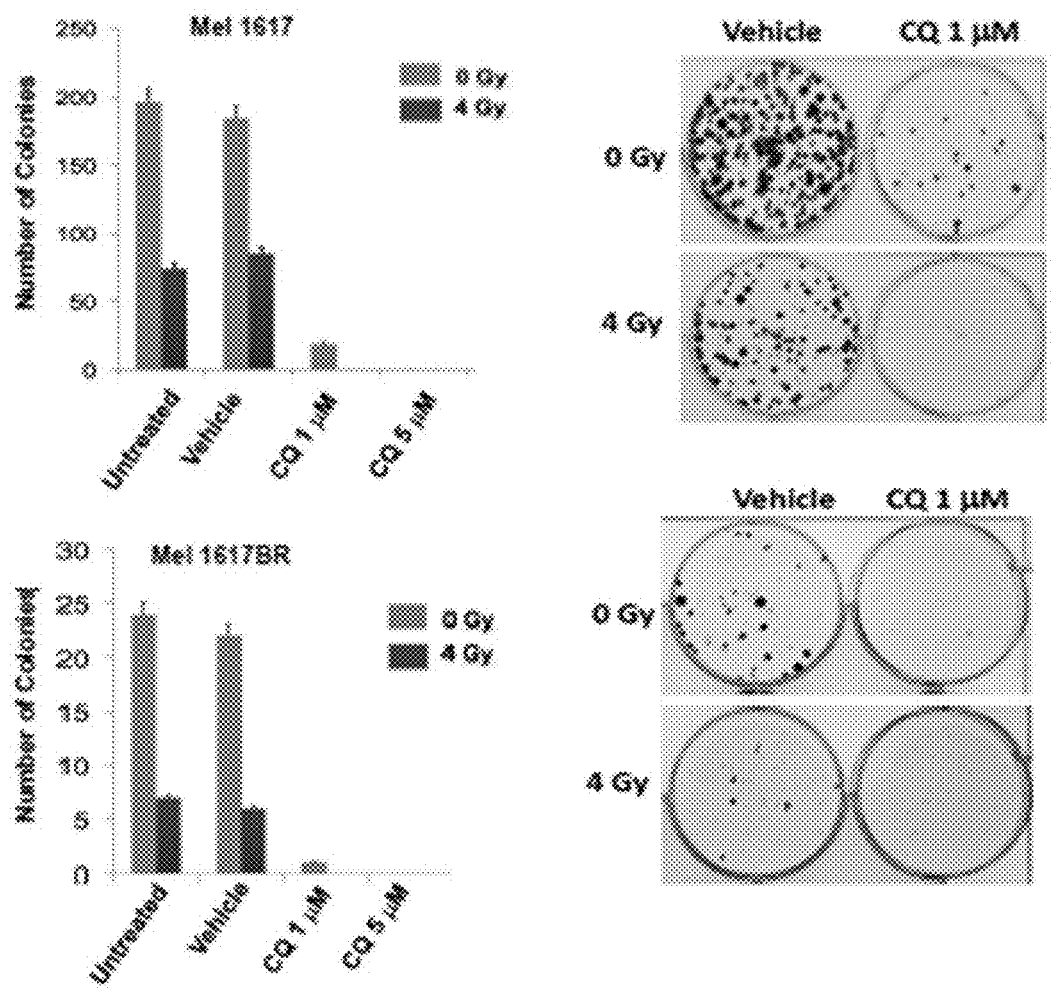
FIG. 11B demonstrates that treatment of Mel 1617 and Mel 1617BR melanoma cells with radiation and CQ has an unexpected greater than additive effect in inhibiting growth and proliferation.

A549 lung cancer cells stably transfected with either non-specific control shRNA or Par-4 shRNA were exposed to 0, 2, 4 Gy of radiation respectively and treated with 10 μM or 20 μM CQ. FIG. 11A demonstrates treatment with radiation and CQ has an unexpected greater than additive effect in inhibiting growth and proliferation (FIG. 11A). The A549 shPar-4 cells showed reduced radiosensitivity and increased growth rate indicating that the action of CQ was dependent on Par-4.

Mel 1617 and Mel 1617BR melanoma cancer cells were treated with either vehicle or 1 μM or 5 μM CQ and were exposed to 0 and 4 Gy of radiation respectively (FIG. 10B). The Mel 1617 and Mel 1617BR cells showed increased radiosensitivity and decreased growth rate, indicating that the combination treatment with CQ and ionizing radiation has an unexpected greater than additive effect in inhibiting growth and proliferation of melanoma cells.

Example 9

The results presented herein demonstrate that ibuprofen and/or curcumin in combination with chloroquine further enhance Par-4 secretion over secretion obtained by any of ibuprofen, curcumin, or chloroquine alone.

To determine whether curcumin or ibuprofen enhanced the secretion of Par-4 in cells treated with chloroquine, MEFs were treated with chloroquine (25 μM), curcumin (5 μM and 10 μM) or ibuprofen (500 μM or 750 μM) or combinations of chloroquine and curcumin or ibuprofen for 24 hours at 37° C.

The conditioned medium (CM), as well as the whole-cell lysates, were subjected to Western blot analysis with the antibodies specific for Par-4, Collagen (Col1A1), albumin, or actin. Col1A1 served as a loading control for protein secretion, as it is generally unchanged in response to the treatments. The samples were also subjected to SDS/PAGE and Coomassie blue staining to determine albumin levels in serum from the CM as another loading control.

Figure 5:
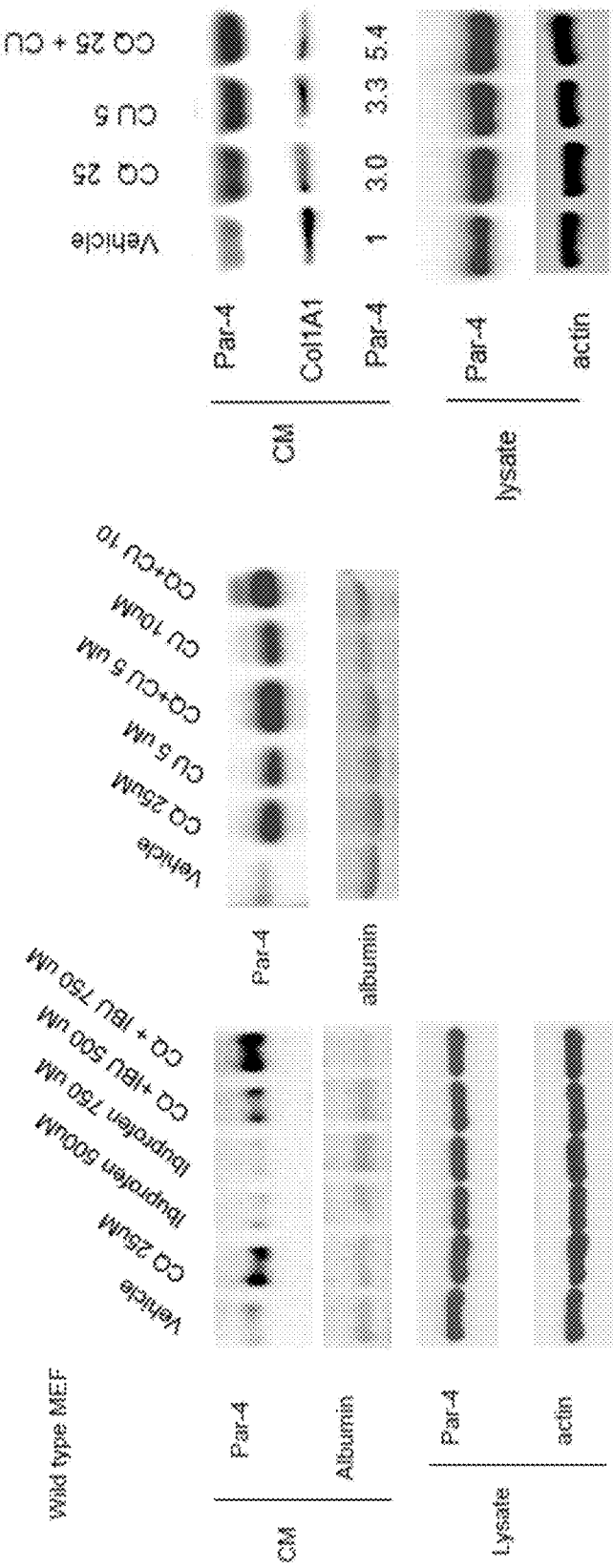
FIG. 5 depicts enhanced secretion of Par-4 in cells treated with both chloroquine and curcumin or ibuprofen.

As can be seen in FIG. 5, treatment with ibuprofen alone does not enhance the production or secretion of Par-4 from MEFs. However, surprisingly ibuprofen at 750 μM significantly improves the secretion of Par-4 achieved by treatment of the MEFs with chloroquine alone.

FIG. 5 also demonstrates that treatment with curcumin alone enhances Par-4 secretion. The combination of chloroquine and curcumin also improves secretion of Par-4 in comparison to treatment with chloroquine or curcumin alone.

The culture media of the treated MEFs secreting elevated levels of Par-4 were assayed for their ability to induce apoptosis in cancer cells in culture. The assays confirmed sufficient Par-4 was secreted to induce enhanced apoptosis of cancer cells.

Materials

Cells and Plasmids

Human lung cancer cells A549, H460, H1299, HOP92, mouse lung cancer cells LLC1, human prostate cancer cells LNCaP, DU145, PC-3, and primary human lung fibroblast cells HEL and epithelial cells HBEC and BEAS-2B were from ATCC, MD; C4-2B cells were from Leland Chung (Ceder Sinai Medical Center, LA), normal human prostate stromal cells PrS and prostate epithelial cells PrE were from Lonza Inc., Allendale, N.J. KP7B cells were from Tyler Jacks, MIT, MA. Par-4$^{+/+}$ and Par-4$^{-/-}$ MEFs were derived from wild type and Par-4-null C57BL/6 mice (Sato et al., 2014 *J Cell Sci* 127:422-431).

Antibodies and siRNA Duplexes

Par-4 (R334) for Western blot or ICC; GRP78 (N20), Col1A1 (H-197), UACA, and pan-cytokeratin (C11) antibodies were from Santa Cruz Biotechnology, Inc. Active caspase 3 antibody (Asp175) (5A1E) and p53 antibody (1C12) were from Cell Signaling. The β-actin antibody was from Sigma Chemical Corp. UACA, Rab 8b (ab124356, rabbit) and Rab8a (ab188574, rabbit) antibodies were from Abcam (Cambridge, Mass.). Active caspase 3 antibody (Asp175) (5A1E) and p53 antibody (1C12) were from Cell Signaling. The β-actin antibody was from Sigma Chemical Corp. Rab8b siRNA duplexes were from Dharmacon (D), and pools of Rab8b siRNA and scrambled siRNA duplexes were from SantaCruz Biotechnology (SC). Human GFP tagged Rab8B (RG204651), and mouse GFP tagged Rab8b (MG202204) were from Origene Technologies, MD.

MEFs were treated with CQ (25 μM) or vehicle (V) for 24 h and mRNA prepared from the cells was examined by Real-Time quantitative reverse transcription PCR (qRT-PCR) for Par-4. The data were normalized relative to a GAPDH control. (see FIG. 8C).

Co-Immunoprecipitation and Western Blot Analysis

Proteins extracted from cell lysates were resolved by SDS-PAGE, and subjected to Western blot analysis as described (Yu et al. (2009) "The regulation of the endosomal compartment by p53 the tumor suppressor gene". *FEBS J* 276, 2201-2212.

Reporter Assays, Apoptosis Assays and Detection of Cell Surface GRP78

To determine the effect of CQ on NF-κB dependent transcription, cells were transfected with NF-κB reporter construct or minimal-promoter-luciferase vector along with β-galactoside construct and then treated with CQ or vehicle.

After 24 h, cell lysates were quantified for luciferase activity, which was normal relative to the corresponding β-galactoside activity. Apoptotic nuclei were identified by immunocytochemical (ICC) analysis for active caspase-3, and nuclei were revealed by 4, 6-diamidino-2-phenylindole (DAPI) staining (Donehower et al. (1992). "Mice deficient for p53 are developmentally normal but susceptible to spontaneous tumours". Nature 356, 215-221, and; el-Deiry et al. (1992) "Definition of a consensus binding site for p53". Nat Genet 1, 45-49). A total of three independent experiments were performed; and approximately 500 cells were scored in each experiment for apoptosis under a fluorescent microscope. Cell surface GRP78 expression on the cancer cell surface was quantified by FACS analysis in the Flow Cytometry Shared Resource Facility, Markey Cancer Center as previously described (Donehower et al. (1992)).

To determine the effect of CQ on p53-dependent transcription or NF-κB-dependent transcription, MEFs (p53+/+ or p53-/-) were transiently co-transfected with p53-response element-luciferase reporter PG13-luc (PG13-luc containing p53 binding sites) or mutant response element-luciferase reporter MG15-luc (MG15-luc containing mutated binding sites for p53) (from Addgene), or NF-κB-luciferase reporter construct, respectively, or with minimal-promoter-luciferase vector pGL3 as control, along with β-galactoside construct. The transfectants were treated with CQ (25 µM) or vehicle for 24 h, luciferase activity was determined and normalized to corresponding β-galactosidase activity and expressed as relative luciferase activity units. After 24 h, cell lysates were quantified for luciferase activity, which was normalized relative to the corresponding β-galactoside activity, as described (Burikhanov et al., 2009 Cell 138: 377-388). Cell cycle distribution was accessed using propidium iodide staining of wild type or p53-null MEFs treated with CQ or vehicle in a Becton-Dickinson LSRII flow cytometer. CQ induced luciferase activity from the p53-reporter luciferase construct but not from a luciferase construct containing mutant response element in p53+/+ MEFs. By contrast, CQ failed to induce luciferase activity in p53-/- MEFs. (see FIG. 8A)

Apoptotic cells were identified by immunocytochemical (ICC) analysis for active caspase-3, and apoptotic nuclei were revealed by 4, 6-diamidino-2-phenylindole (DAPI) staining (Burikhanov et al., 2014b Nature Chem Biol 10:924-926). A total of three independent experiments were performed; and approximately 500 cells were scored in each experiment for apoptosis under a fluorescent microscope.

Animal Experiments

C57BL/6 mice were injected via the intraperitoneal (i.p.) route with a single injection of CQ (50 mg/kg body weight) or corn oil vehicle, and whole-blood samples were collected 24 h later. Serum was separated from the blood samples, heated at 56° C. to inactivate complement. Aliquots of the mouse serum samples were added to the growth medium (final 20% mouse serum) of normal and cancer cells in culture and tested for induction of ex vivo apoptosis in cancer cells.

To test the effect of CQ on metastatic tumor growth, LLC1/luciferase cells ($0.5 \times 10^6$ cells) were injected via the tail vein in C57BL/6 mice and 24 h later, the mice were injected i.p. with CQ (25 mg/kg body weight) injection given daily for five consecutive days. Serum from the mice was examined 24 h after the 5th CQ injection for p53, p21, PIG3, Par-4, and actin by Western blot analysis (see FIG. 8B). The mice were imaged for luciferase expression after 10 days as previously described and humanely killed to examine their tumors at day 21, as previously described (Zhao et al. Cancer Biol Ther 12:152-157, 2011. PMCID: PMC3154287).

All animal procedures were performed with University of Kentucky IACUC approval. Primers used for Real-Time quantitative reverse transcription PCR (qRT-PCR) assay The primers used were: mRab8a Forward: 5'-CTGGCACTCGACTATGGGAT-3' SEQ ID NO: 4; mRab8a Reverse: 5'-TTTGCTTTGATATCCCTGGC-3' SEQ ID NO: 5; mRab8b Forward: 5'-CACGCCTCTTCAGATGTTGA-3' SEQ ID NO: 6; mRab8b Reverse: 5'-CGACTTTGCACTTGTCTCCA-3' SEQ ID NO: 7; mouse Par-4 Forward: 5'-AGAATGAAGCTGCGACCCTC-3'; SEQ ID NO: 8 mouse Par-4 Reverse: 5'-ATCTTCTGGGGC ACTGGTTG-3' SEQ ID NO: 9; and internal control primers for mGAPDH Forward: 5'-GTGAGGCAAAAGGGAAGGTG-3' SEQ ID NO: 10; mGAPDH Reverse: 5'-AGGCATGGCAGAT-TCAG AGT-3' SEQ ID NO: 11.

Statistical Analysis

All experiments were performed in triplicate to verify the reproducibility of the findings. The results show a mean of at least 3 experiments±Standard Deviation (s.d.). Statistical analyses were carried out with Statistical Analysis System software (SAS Institute, Cary, N.C.) and P values were calculated using the Student's t-test.

The foregoing results demonstrate that CQ induced significantly elevated levels of Par-4 systemically in mice and in patients following CQ treatment, and these Par-4 levels were adequate to induce paracrine apoptosis of diverse prostate and lung cancer cells. Importantly, CQ inhibited the growth of tumors in a Par-4-dependent manner. Collectively, CQ induces paracrine effects via Par-4 secretion from normal cells leading to tumor cell apoptosis and tumor growth inhibition.

While certain exemplary embodiments have been described and shown in the accompanying figures, it is to be understood that such embodiments are merely illustrative of and not restrictive on the broad invention, and that this invention need not be limited to the specific constructions and arrangements shown and described, since various other modifications may occur to those ordinarily skilled in the art.

I claim:

1. A method of treating a p53-deficient human lung or prostate cancer cell that is nonresponsive to chloroquine, or salt or prodrug thereof, said method comprising contacting a population of human lung or prostate cancer cells comprising the p53-deficient human lung or prostate cancer cell that is nonresponsive to chloroquine, or salt or prodrug thereof, and normal cells that are responsive to chloroquine, or salt or prodrug thereof, with about 100 nM to about 25 μM of chloroquine, or salt or prodrug thereof, wherein such treatment induces Par-4 production by the normal cells that are responsive to chloroquine, wherein the p53-deficient human lung or prostate cancer cell is killed, cancer cell proliferation is inhibited, cancer cell metastasis is inhibited, and/or recurrence of one or more tumors comprising the p53-deficient human lung or prostate cancer cell is inhibited.

2. The method of claim 1, wherein the chloroquine or salt or prodrug thereof is chloroquine phosphate, chloroquine diphosphate, or hydroxychloroquine.

3. The method of claim 1, wherein the p53-deficient human lung or prostate cancer cell is a p53-deficient human prostate cancer cell.

4. The method of claim 1, wherein the p53-deficient human lung or prostate cancer cell is a p53-deficient human lung cancer cell.

5. The method of claim 1, wherein the method further comprises contacting the normal cells with an effective amount curcumin.

6. The method of claim 1, wherein the method further comprises contacting the normal cells with an effective amount of ibuprofen.

7. The method of claim 1, wherein the method further comprises administering an effective amount of ionizing radiation to the cancer cell.

8. The method of claim 1, wherein the chloroquine is not co-administered with a chemotherapeutic.

9. A method of inhibiting p53-deficient human lung or prostate cancer cell proliferation, lung or prostate cancer cell metastasis, and/or recurrence of lung or prostate tumors in a subject comprising administering about 100 nM to about 25 μM of chloroquine phosphate, chloroquine diphosphate, hydroxychloroquine, or salt or prodrug thereof to a subject in need thereof, wherein the chloroquine phosphate, chloroquine diphosphate, hydroxychloroquine, or salt or prodrug thereof is not co-administered with a chemotherapeutic, and wherein prostate apoptosis responsive 4 (Par-4) secretion from normal cells in the subject is increased.

10. The method of claim 9, wherein the p53-deficient human lung or prostate cancer cell is a p53-deficient human prostate cancer cell.

11. The method claim 9, wherein the lung or prostate cancer cell is a p53-deficient human lung cancer cell.

12. The method of claim 9, wherein the chloroquine phosphate, chloroquine diphosphate, hydroxychloroquine, or the salt or the prodrug thereof is administered in a divided dose twice daily.

13. The method of claim 9, wherein the method further comprises administering ionizing radiation to the cancer cell, wherein the chloroquine phosphate, chloroquine diphosphate, hydroxychloroquine, or salt or prodrug thereof sensitizes the cancer cell to the ionizing radiation.

\* \* \* \* \*